United States Patent
Agee et al.

(10) Patent No.: US 11,400,061 B2
(45) Date of Patent: Aug. 2, 2022

(54) ONYCHOMYCOSIS TREATMENT COMPOSITIONS AND METHODS

(71) Applicant: Hallux Inc., Laguna Hills, CA (US)

(72) Inventors: Christopher Ronald Agee, Lake Forest, CA (US); Robert L. Orr, San Clemente, CA (US); Thomas Mark Tremblay, San Francisco, CA (US)

(73) Assignee: HALLUX INC., Laguna Hills, CA (US)

( * ) Notice: Subject to any disclaimer, the term of this patent is extended or adjusted under 35 U.S.C. 154(b) by 0 days.

(21) Appl. No.: 17/474,656

(22) Filed: Sep. 14, 2021

(65) Prior Publication Data

US 2021/0401778 A1    Dec. 30, 2021

Related U.S. Application Data

(63) Continuation of application No. PCT/US2020/054710, filed on Oct. 8, 2020.

(60) Provisional application No. 62/912,494, filed on Oct. 8, 2019.

(51) Int. Cl.

| | | |
|---|---|---|
| *A61K 31/137* | (2006.01) | |
| *A61K 9/00* | (2006.01) | |
| *A61K 47/10* | (2017.01) | |
| *A61K 47/14* | (2017.01) | |
| *A61K 47/38* | (2006.01) | |

(52) U.S. Cl.
CPC .......... *A61K 31/137* (2013.01); *A61K 9/0014* (2013.01); *A61K 47/10* (2013.01); *A61K 47/14* (2013.01); *A61K 47/38* (2013.01)

(58) Field of Classification Search
CPC ...... A61K 9/0014; A61K 47/10; A61K 47/14; A61K 47/38
See application file for complete search history.

(56) References Cited

U.S. PATENT DOCUMENTS

| | | |
|---|---|---|
| 9,446,009 B2 | 9/2016 | Kochinke et al. |
| 9,931,282 B2 | 4/2018 | Restrepo et al. |
| 2004/0062733 A1 | 4/2004 | Birnbaum |
| 2006/0165747 A1 | 7/2006 | Rolf |
| 2007/0014743 A1 | 1/2007 | Birnbaum |
| 2007/0196325 A1 | 8/2007 | Zhang et al. |
| 2010/0048724 A1 | 2/2010 | Birnbaum et al. |
| 2013/0210925 A1 | 8/2013 | Birnbaum et al. |
| 2014/0322293 A1 | 10/2014 | Kochinke et al. |
| 2015/0342871 A1* | 12/2015 | Buyuktimkin ....... A61K 9/0014 514/655 |
| 2018/0311163 A1 | 11/2018 | Thuresson et al. |

FOREIGN PATENT DOCUMENTS

WO    2017163091 A1    9/2017

OTHER PUBLICATIONS

Alio S, et al., "Dermatophytes growth curve and in vitro susceptibility test: a broth microtitration method," Medical Mycology, Jun. 2005; 43(4):319-325.
Bhatt et al., "Efinaconazole Topical Solution, 10%: Formulation Development Program of a New Topical Treatment of Toenail Onychomycosis," Journal of Pharmaceutical Sciences, 2015; 104:2177-2182.
Bristow et al., "Rapid Treatment of Subungual Onychomycosis Using Controlled Micro Nail Penetration and Terbinafine Solution," J Drugs Dermatol., 2016; 15(8):974-978.
Canavan et al., "Subungual Space: The Next Frontier," Skin Appendage Disord, 2019; 5:50-51.
Dolton, et al., "Terbinafine in Combination with Other Antifungal Agents for Treatment of Resistant or Refractory Mycoses: Investigating Optimal Dosing Regimens Using a Physiologically Based Pharmacokinetic Model," Antimicrob. Agents Chemother., 2014; 58(1):48-54.
Elewski, Boni E., "Study Evaluating the Effect of Jublia on Dermatophytomas," Jan. 2018; 10 pgs. NIH—U.S. National Library of Medicine, ClinicalTrials.gov. Retrieved from https://clinicaltrials.gov/ct2/show/NCT03098615?cond=onychomycosis&draw=13&rank=100.
Elewski, et al., "Access of Efinaconazole Topical Solution, 10%, to the Infection Site by Spreading Through the Subungual Space," Journal of Drugs in Dermatology, Nov. 2014; 13(11):1394-1398.
Geyer, et al., "Modulation of linear nail growth to treat diseases of the nail," J Am Acad Dermaol., Feb. 2004; 50(2):229-234.
Ghannoum et al., "Fungal Nail Infections (Onychomycosis): A Never-Ending Story?" PLOS Pathog, Jun. 2014; 10(6):e1004105; 6 pgs. https://doi.org/10.1371/journal.ppat.1004105.
Goodfield et al., "Combined treatment with surgery and short duration oral antifungal therapy in patients with limited dermatophyte toenail infection," J Dermatol Treat, 2000; 11:259-262.
International Search Report and Written Opinion for International Application No. PCT/US20/54710 dated Feb. 11, 2021; 19 pgs.
Jublia (efinaconazole) topical solution, 10%, FDA Prescribing Information by Valean Pharmaceuticals North America LLC, Bridgewater, New Jersey 08807; Issued Jun. 2014; 13 pgs.

(Continued)

*Primary Examiner* — Genevieve S Alley
(74) *Attorney, Agent, or Firm* — Umberg Zipser LLP

(57) ABSTRACT

Compositions and methods are presented that provide substantially improved physical and pharmacological parameters for subungually administrable formulations. Most beneficially, the compositions presented herein have a viscosity and film-forming capacity that retain the liquid formulation in sufficient quantities and that help penetrate the polysaccharide matrix commonly associated with onychomycosis. In especially preferred aspects, the carrier is formulated to have a high concentration of the active pharmaceutically active agent (API), to allow migration of the formulation within the subungual space, and to reduce systemic absorption while promoting diffusion of the API into the nail plate at or above minimum inhibitory concentration into a larger treatment space.

17 Claims, 8 Drawing Sheets

(56) References Cited

OTHER PUBLICATIONS

Kathe et al., "Film forming systems for topical and transdermal drug delivery," Asian Journal of Pharmaceutical Sciences, 2017; 12:487-497.

Leeyaphan et al., "Dermatophytoma: An under-recognized condition," Indian J Dermatol Venereol Leprol., 2016; 82:188-9. Retrieved from http://www.ijdvl.com/text.asp?2016/82/2/188/165539.

McAuley et al., "An investigation of how fungal infection influences drug penetration through onychomycosis patient's nail plates," European Journal of Pharmaceutics and Biopharmaceutics, 2016; 102:178-184.

Osborne et al., "Antifungal drug response in an in vitro model of dermatophyte nail infection," Medical Mycology, Apr. 2004; 42:159-163.

Pollak et al., "Efinaconazole Topical Solution, 10%: Factors Contributing to Onychomycosis Success," J. Fungi, 2015; 1:107-114.

Pollak et al., "The Impact of New Topical Antifungals on Onychomycosis Management," Oct. 2017; 30(10); 12 pgs. Retrieved from https://www.podiatrytoday.com/impact-new-topical-antifungals-onychomycosis-management.

Schafer-Korting et al., "Fungicidal Activity Plus Reservoir Effect Allow Short Treatment Courses with Terbinafine in Tinea pedis," Skin Pharmacol Physiol 2008; 21:203-210.

Seebacher, Claus, "Action mechanisms of modern antifungal agents and resulting problems in the management of onychomycosis," Mycoses, 2003; 46:506-510.

Vlahovic, Tracey C., "Differentiating Nail Diseases With Dermoscopy," Podiatry Today, Dec. 2018; 31(12):20-25.

Vlahovic, Tracey, "When a Patient Presents With Linear Streaks In A Nail," Podiatry Today, Nov. 2015; 28(12):20-24.

Zaias, MD et al., "The Successful Treatment of Trichophyton rubrum Nail Bed (Distal Subungual) Onychomycosis With Intermittent Pulse-Dosed Terbinafine," Arch Dermatol., 2004; 140:691-695.

\* cited by examiner

US 11,400,061 B2

ONYCHOMYCOSIS TREATMENT COMPOSITIONS AND METHODS

This application is a continuation of our copending International Application with the serial number PCT/US2020/054710, filed Oct. 8, 2020, which claims priority to US Provisional Patent Application with the Ser. No. 62/912,494, which was filed Oct. 8, 2019, and which is incorporated by reference herein.

FIELD OF THE INVENTION

The present disclosure relates to compositions and methods of treatment of the subungual space, especially as it relates to treatment of onychomycosis and/or dermatophytoma.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Onychomycosis is a fairly common infection of the nail bed. Due to the location of the infection, delivery of sufficiently high (therapeutically effective) concentrations of antifungal agents has been difficult. Moreover, as a fungal infection includes dividing cells as well as spores, therapeutically effective concentrations are relatively high, even where relatively potent agents are employed. For example, terbinafine is a potent antifungal agent, approved for treatment of onychomycosis in oral form. While the oral form has been somewhat effective in treatment of the disease due to systemic delivery of drug to the soft tissue under the nail (nail bed) where the disease-causing dermatophytes proliferate, treatment success is often limited due to the systemic (especially hepatic) toxicity of terbinafine. Indeed, monotherapy was shown to be associated with a high rate of failure due to low local drug concentration and need for a high minimum inhibitory concentration (MIC) in the nail plate (see e.g., *Mycoses* 2003, 46, 506-510). To improve efficacy, administration of terbinafine may be accompanied by surgery to increase cure rates (*Journal of Dermatological Treatment* (2000) 11, 259-262). However, such treatment requires nail plate removal which is less than desirable. In an effort to mitigate toxicity, intermittent pulsed doses of 250 mg/day for 7 days every 2-4 months were implemented with at least some improvement in outcome (see e.g., *Arch Dermatol* Vol 140, June 2004, p 691-695). However, cure rates were still less than desirable and potential toxicity issues remained.

To avoid problems associated with high systemic exposure, antifungal drugs can be topically applied to the nail plate. For example, an alcoholic solution of 10% efinaconazole (marketed as JUBLIA™) has been developed. Unfortunately, fairly low penetration of the nail plate led to only modest complete cure rates between 15.2% and 17.8% of treated population (see FDA Prescribing Information).

More recently, subungual administration has been proposed as a means to deliver antifungal agents to the site of infection, and exemplary compositions and methods are described in US 2013/0210925. For example, US 2010/0048724 and U.S. Pat. No. 9,446,009 teach non-liquid terbinafine HCl salt compositions for direct administration to the subungual space, and U.S. Pat. No. 7,135,194 teaches solid or semi-solid formulations for subungual administration. In still further example, semi-solids can be used for subungual delivery as described in US 2004/0062733 and US 2007/0014743. However, while relatively high drug concentrations can be locally administered, delivery of terbinafine from the solid or semi-solid carrier often fails to facilitate diffusion of the active agent to adjacent areas. Moreover, such solid or semi-solid carriers also often will not promote diffusion of the active agent into the nail bed and nail plate. Therefore, the carrier will typically need to be inserted into the leading edge of the diseased area which leads in many cases to trauma and punctile bleed, resulting in lifting of the nail plate.

In yet further attempts to reach the site of infection, a fluorescence labeled alcoholic solution similar to that of efinaconazole was applied to the hyponychium and the distal end of the toenail to so spread the solution below the surface of the nail and distal skin area. Notably, some of the applied solution appeared to penetrate via the hyponychium to locations between the nail bed and nail plate, with some of the solution adhering to the nail plate (see *J Drugs Dermatol* 2014, Vol. 13, No. 11, 1394-8). However, no antifungal agent was used and as such antifungal activity was not assessed. Given the relatively low concentration of efinaconazole and relatively small diffused volume of the vehicle, antifungal treatment efficacy using such low concentration formulations is uncertain at best.

Compounding the difficulties with known subungual administration is the presence of a polysaccharide matrix that is produced by the fungal mass, which presents itself as "dermatophytoma". Indeed, where the polysaccharide matrix is extensive, decreased penetration of antifungal agents makes the condition resistant to standard antifungal therapy, and surgical removal of the nail plate in combination with oral terbinafine is often the only somewhat effective manner of treatment.

In addition, it is difficult to maintain effective antifungal concentration for the duration of the time required for a nail to grow out in a healthy manner and appearance to achieve a complete cure. Nails grow at approximately 1 mm/month, and it takes about 12 months for a nail to grow out. As a consequence, a longer lasting depot of an antifungal drug to achieve high local doses would be more effective. Unfortunately, the concentrations of currently known antifungal agents will typically not achieve such high local doses. Moreover, it should be appreciated that 1000-times higher concentrations of antifungal agent are needed to eradicate fungal spores in the dormant phase (see e.g., *Mycoses* (2002) 46, 506-510).

Thus, even though various compositions and methods are known in the art, all or almost all of them have various disadvantages. Consequently, there is a need to provide improved compositions and methods that provide effective treatment to the subungual space, particularly as it relates to treatment of onychomycosis and/or dermatophytoma.

SUMMARY OF THE INVENTION

Compositions and methods for treatment of onychomycosis and/or dermatophytoma are presented in which a pharmaceutical composition with controlled physicochemical parameters is employed that maximizes the subungual treatment area, local concentration and retention of a therapeutic agent, which is in most cases an antifungal agent. Advantageously, contemplated compositions will also exhibit (1) high adherence and penetration into the polysaccharide matrix that is often associated with dermatophytoma, (2) high local dose and duration of effective drug availability, and (3) high secondary diffusion in the nail plate and nail bed accompanied by low systemic adsorption of the therapeutic agent. Further, the compositions may be clinically administered employing a method that does not induce pain and/or trauma, and at a dose that does not give concern for toxic side effects.

In one aspect, the inventors contemplate a liquid pharmaceutical composition that includes a pharmaceutically acceptable carrier (vehicle) comprising a hydrophobic solvent, an optional polymeric film-forming agent, and an antifungal agent. Most typically, the antifungal agent is dissolved in the pharmaceutically acceptable carrier and present at a concentration of at least 10 wt % (and more preferably at least 20%, and even more preferably at least 40%). A polymeric film forming agent may be included in the composition to provide a preferred viscosity of between about 500-2,500 cP (mPa*s), and more preferably between about 750-1,500 cP (mPa*s).

For example, in some embodiments the hydrophobic solvent is benzyl alcohol, benzyl benzoate, isostearic acid, diisopropyl adipate, diethyl sebacate, and/or isopropyl myristate, suitable hydrophilic solvents include propylene carbonate, dimethyl isosorbide, and/or lactic acid, and suitable film-forming agents include ethyl lactate, triethyl citrate, dimethyl-, diethyl- or dibutyl-phthalate, and/or a substituted polymeric cellulose. With regard to suitable antifungal agents it is contemplated that the antifungal agent can be an allylamine antifungal drug, a morpholine antifungal drug, a polyene antifungal drug, and/or an azole antifungal drug. Among other agents, preferred antifungal agents are allylamine antifungal drugs and especially terbinafine.

In other examples, the antifungal agent may be present at a concentration of at least 20 wt % or at least 40 wt % and is stable for at least 4 weeks (or at least 12 weeks, or at least 6 months) when the composition is stored at 25° C. and 60% relative humidity. Therefore, the hydrophobic solvent may comprise in some embodiments isostearic acid, isopropyl myristate and/or diisopropyl adipate, and may further include dimethyl isosorbide, propylene carbonate, lactic acid, or benzyl alcohol. Moreover, preferred polymeric film forming agents especially include triethyl citrate and ethyl cellulose. It is further contemplated that where the antifungal agent is terbinafine, the antifungal agent is terbinafine in free-base form.

Therefore, and viewed from a different perspective, the inventors also contemplate a high-dose antifungal liquid pharmaceutical composition that includes a pharmaceutically acceptable carrier comprising a hydrophobic solvent, a polymeric film forming agent, and an antifungal agent at a concentration of at least 30 wt % of the composition. Most typically, the antifungal agent is dissolved in the pharmaceutically acceptable carrier and is stable for at least 4 weeks (or at least 12 weeks, or at least 6 months) when the composition is stored at 25° C. and 60% relative humidity, and the pharmaceutical composition has a viscosity of between about 500-2,500 cP (mPa*s), or more preferably between about 750-1,500 cP (mPa*s).

In further contemplated embodiments, the antifungal agent is present at a concentration of at least 40 wt % of the composition, while preferred hydrophobic solvents include benzyl alcohol, isostearic acid, diisopropyl adipate, diethyl sebacate, and isopropyl myristate, and where used, preferred hydrophilic solvents include dimethyl isosorbide, propylene carbonate, and lactic acid. It is further preferred that the polymeric film forming agent comprises a substituted cellulose. Most typically, the antifungal agent is an allylamine antifungal drug, and a morpholine antifungal drug, a polyene antifungal drug, or an azole antifungal drug, and most preferably terbinafine in free base form.

In yet a further aspect of the inventive subject matter, the inventors contemplate a method of providing treatment into a subungual space in a mammal that includes a step of administering a liquid pharmaceutical composition to a subungual space located between the nail plate and the nail bed. Most typically, the pharmaceutical composition comprises a pharmaceutically acceptable carrier that includes a hydrophobic solvent in which a therapeutic agent is dissolved, and an optional polymeric film forming agent, wherein the pharmaceutical composition has a viscosity of between about 500-2,500 cP (mPa*s). Moreover, it should be noted that in such methods the therapeutic agent is present in the pharmaceutical composition in an amount that ascertains a minimum therapeutic concentration of the therapeutic agent in the subungual space and preferably also the treatment space. Most typically, the therapeutic agent is present in the pharmaceutical composition in an amount that ascertains a minimum inhibitory concentration of the therapeutic agent in the subungual space and a treatment space that extends beyond the subungual space. The use of high-concentration liquid formulations is particularly desirable as access to the treatment space, when using solid implants, was accompanied with bleed and trauma. In contrast, high-concentration liquid formulations can distribute throughout the subungual space and allow for diffusion of the active agent into the treatment space at MIC.

While not limiting to the inventive subject matter, it is generally preferred that the step of subungual administration of the liquid pharmaceutical composition comprises a step of atraumatically inserting a cannula between the nail plate and the nail bed and another step of administering the liquid pharmaceutical composition through the cannula. Preferably, but not necessarily, the cannula is a blunt-tip cannula having at least one lateral opening in a distal portion of the cannula. Moreover, it is noted that the subungual space will typically include an area infected with a fungus where the nail plate has partially detached from the nail bed (onycholysis), and wherein the therapeutic agent is an antifungal agent. However, it should be noted that the liquid pharmaceutical composition need not be directly delivered to the infected area, but that the liquid pharmaceutical composition may also passively migrate to the infected area by action of both translation and diffusion. Advantageously, the step of administering the liquid pharmaceutical composition also ascertains the minimum therapeutic concentration of the therapeutic agent in the nail bed and nail plate. In further advantageous aspects, it should be recognized that the compositions contemplated herein will have the antifungal agent at concentrations well exceeding the MIC to so provide a longer period of antifungal protections, and in some cases be even toxic to dormant spores.

In some embodiments, the hydrophobic solvent, relative to dimethyl sulfoxide (DMSO) or dimethyl formamide (DMF), reduces absorption of the therapeutic agent into the systemic circulation and increases availability of the therapeutic agent to the nail bed and its surface. Most typically, between 10 and 100 μL of the liquid pharmaceutical composition will be injected into the subungual space. It should also be appreciated that in most embodiments gentle, non-traumatic mechanical piercing action of the blunt-tip cannula penetrates into a porous polysaccharide matrix produced by a dermatophyte, the liquid form allows for lateral flow through the porous matrix, and a polymeric film forming agent and/or that the viscosity of the liquid pharmaceutical composition allows for lateral flow within the subungual space, typically without being expressed excessively and lost from the subungual space. Therefore, it should be noted that the viscosity of exemplary liquid pharmaceutical composition will allow for retention of at least 80% of an administered volume of the liquid pharmaceutical composition in the subungual space.

Most preferably, the hydrophobic solvents will be isostearic acid, benzyl alcohol, diisopropyl adipate, diethyl sebacate, and/or isopropyl myristate, and suitable hydrophilic solvents will be dimethyl isosorbide, propylene carbonate, and/or lactic acid, and the polymeric film forming agent will be a substituted cellulose (e.g., ethyl cellulose), and/or the therapeutic agent will be an antifungal agent such as an allylamine antifungal drug, a morpholine antifungal drug, a polyene antifungal drug, and/or an azole antifungal drug.

In another aspect of the inventive subject matter, the inventors also contemplate a method of treating onychomycosis that includes a step of subungual administration of a liquid pharmaceutical composition comprising a pharmaceutically acceptable carrier that includes a hydrophobic solvent, an optional hydrophilic solvent, an optional polymeric film forming agent, and an antifungal agent. The antifungal agent is preferably dissolved in the pharmaceutically acceptable carrier and present at a concentration of at least 10 wt %, and the pharmaceutical composition has a viscosity of between about 500-2,500 cP (mPa*s). Most typically, the antifungal agent is present in the pharmaceutical composition in an amount that ascertains a minimum inhibitory concentration of the antifungal agent in the subungual space and a treatment space that extends beyond the subungual space.

As noted before, it is contemplated that the hydrophobic solvent may be isostearic acid, benzyl alcohol, diisopropyl adipate, diethyl sebacate, and/or isopropyl myristate, the hydrophilic solvent may be dimethyl isosorbide, propylene carbonate, and/or lactic acid, and that the polymeric film forming agent comprises a substituted cellulose, and/or that the antifungal agent is an allylamine antifungal drug (most preferably terbinafine), a morpholine antifungal drug, a polyene antifungal drug, and/or an azole antifungal drug.

In some embodiments, the antifungal agent is present at a concentration of at least 20 wt % and stable for at least 4 weeks when the composition is stored at 25° C. and 60% relative humidity, or the antifungal agent is present at a concentration of at least 40 wt % and stable for at least 4 weeks when the composition is stored at 25° C. and 60% relative humidity. Further, the composition remains stable in a homogeneous flowable form for at least 4 weeks when the composition is stored at 5° C. In other embodiments, the composition has a viscosity of between about 750-1,500 cP (mPa*s). For example, the hydrophobic solvent may comprise isopropyl myristate and/or diisopropyl adipate, and optionally benzyl alcohol, and the antifungal agent is terbinafine free base.

Therefore, the inventors also contemplate a method of treating dermatophytomas that includes a step of subungually administering a liquid pharmaceutical composition into a polysaccharide matrix located between a nail bed and a nail plate. In such methods, the liquid pharmaceutical composition comprises a pharmaceutically acceptable carrier that includes a hydrophobic and optional hydrophilic solvent, a polymeric film forming agent, and an antifungal agent, and the antifungal agent is dissolved in the pharmaceutically acceptable carrier and present at a concentration of at least 20 wt %, and wherein the pharmaceutical composition has a viscosity of between about 500-2,500 cP (mPa*s).

Most typically, the hydrophobic solvent is benzyl alcohol, isostearic acid, diisopropyl adipate, diethyl sebacate, and/or isopropyl myristate, the hydrophilic solvent is optional and comprises dimethyl isosorbide, propylene carbonate, and/or lactic acid, and the polymeric film forming agent comprises a substituted cellulose, and/or the antifungal agent is an allylamine antifungal drug, and a morpholine antifungal drug, a polyene antifungal drug, or an azole antifungal drug. In such methods, the antifungal agent may be present at a concentration of at least 40 wt % and stable for at least 4 weeks when the composition is stored at 25° C. and 60% relative humidity, and/or the composition may have a viscosity of between about 750-1,500 cP (mPa*s). For example, preferred hydrophobic solvent comprise isostearic acid, isopropyl myristate and/or diisopropyl adipate, and optionally benzyl alcohol, while the antifungal agent is terbinafine free base.

In still another aspect of the inventive subject matter, the inventors contemplate a method of treating onychomycosis that includes a step of subungually administering a liquid pharmaceutical composition through a cannula inserted to location that does not need to contact a visible proximal edge of an area affected by onychomycosis, and where the liquid composition migrates to a visible proximal edge of an area affected by onychomycosis. Most typically, the composition comprises a pharmaceutically acceptable carrier that includes a hydrophobic (and in some cases hydrophilic) solvent, a polymeric film forming agent, and an antifungal agent dissolved in the hydrophobic/hydrophilic solvent mixture, and wherein the pharmaceutical composition has a viscosity of between about 500-2,500 cP (mPa*s). Upon subungual administration, the liquid pharmaceutical composition is then allowed to migrate from the location to at least the visible proximal edge of the area affected by onychomycosis. Most typically, the antifungal agent is present in the pharmaceutical composition in an amount that ascertains a minimum inhibitory concentration of the antifungal agent in a subungual space and a treatment space that extends beyond the subungual space For example, the location (of the cannula) is at least 1 mm, or at least 3 mm away from the visible proximal edge of the area affected by onychomycosis. Moreover, it is generally preferred that the subungual administration uses a step of delivering the liquid pharmaceutical composition through a blunt-tip cannula.

Viewed from yet another perspective, the inventors also contemplate a method of retaining a liquid pharmaceutical composition comprising an antifungal agent in a subungual treatment space that includes a step of subungually administering the liquid pharmaceutical composition into the subungual space. Most typically, the liquid pharmaceutical composition comprises a pharmaceutically acceptable carrier that includes at least a hydrophobic solvent, a polymeric film forming agent, wherein the antifungal agent is dissolved in the pharmaceutically acceptable carrier. Most typically, the liquid pharmaceutical composition has a viscosity of between about 750-1,500 cP (mPa*s) or between about 500-2,500 cP (mPa*s).

Preferably, but not necessarily, at least 80% or at least 90% of the administered volume is retained within the subungual space. As noted above, preferred hydrophobic solvents include benzyl alcohol, isostearic acid diisopropyl adipate, diethyl sebacate, and isopropyl myristate, while a hydrophilic solvent is optional and may be dimethyl isosorbide, propylene carbonate, and/or lactic acid, and the preferred polymeric film forming agent comprises a substituted cellulose (e.g., ethyl cellulose). In most embodiments, the antifungal agent is an allylamine antifungal drug (e.g., terbinafine), a morpholine antifungal drug, a polyene antifungal drug, and/or an azole antifungal drug. Advantageously, the antifungal agent is present at a concentration of at least 20 wt %, or at least 30 wt %, or at least 40 wt %, and stable for at least 4 weeks when the composition is stored at 25° C. and 60% relative humidity. In still further preferred aspects, the antifungal agent is stable at refrigeration below room temperature (e.g., 4-5° C.).

Various objects, features, aspects, and advantages will become more apparent from the following detailed description of preferred embodiments, along with the accompanying drawing.

DETAILED DESCRIPTION

Figure 1:
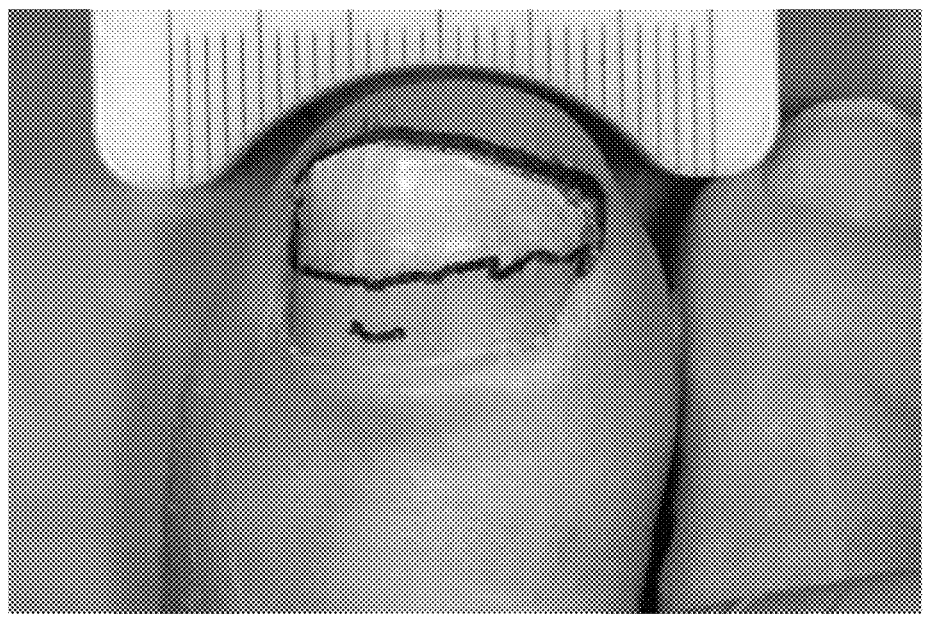
FIG. 1 is a photograph of an exemplary toe nail with onychomycosis.

The inventors have now discovered liquid pharmaceutical compositions for subungual administration that allow for a high concentration of antifungal agent in a pharmaceutically acceptable carrier. Contemplated carriers comprise a hydrophobic solvent, an optional hydrophilic solvent, and an optional polymeric film forming agent, and the pharmaceutical composition has a viscosity that not only allows for targeted delivery to the subungual space via a small-bore cannula, but also allows for lateral, proximal, and distal passive distribution of the liquid pharmaceutical composition through the subungual space, typically via translation, capillary action, and/or surface tension. Advantageously, the compositions presented herein will also allow for diffusion of the antifungal agent into the nail plate at concentrations at or above the MIC while avoiding systemic absorption into the circulatory system of a patient. Moreover, the compositions presented herein also enable the distribution of the pharmaceutical composition into and through the polysaccharide matrix of a dermatophytoma, and consequently are also suitable for treatment of both onychomycosis and dermatophytoma. In this context, it should be noted that the pharmaceutical compositions will be effective as a monotherapy (i.e., will not include a second drug), but that such compositions can include additional therapeutic agents.

As used herein, it is important to recognize that the term "subungual space" refers to a pre-existing void space that is present between the nail bed and the nail plate, and that is a result of fungal growth in people with onychomycosis. Viewed from a different perspective, the subungual space may be considered a contiguous open space that may be empty, or that may include debris from keratin, collagen, and/or fungal material (such as a polysaccharide matrix). Therefore, the subungual space is typically a space of variable geometry that may extend over a significant portion of the nail organ, and that may further include areas that are co-extant with current and/or prior fungal growth. Thus, from a drug administration perspective, the subungual space is a space that is accessible from a location outside the nail organ without damage to or separation of the nail plate and nail bed upon access. For example, administration of a composition as contemplated herein can be performed with a small gauge blunt-tip cannula without producing a punctile bleed and nail plate/nail bed separation.

The term "subungual space" is therefore distinct from the term "treatment space" in that the treatment space will also include areas that are outside the subungual space but in which the active ingredient will be present (e.g., via diffusion), preferably in an amount that is at least the MIC (minimum inhibitory concentration) of the active agent. Consequently, the treatment space in most cases will be more extensive than the subungual space and will include an area that has not directly contacted a treatment composition. For example, the treatment space will typically include a space within which the active ingredient is present due to diffusion and/or nail growth. For example, where a highly concentrated terbinafine solution was atraumatically administered into the subungual space, the treatment space will include space adjacent to the subungual space in which the terbinafine is present in at least MIC and a portion of the nail plate into which the terbinafine has diffused. Notably, such region in the nail plate may continually expand the treatment space as the nail grows distally.

With regard to the term "liquid" as used in conjunction with contemplated compositions herein, it is noted that the term liquid refers to compositions that comprise a liquid component (typically a solvent that is liquid at room temperature) that may have one or more other components (e.g., antifungal agent) dissolved, dispersed, or otherwise distributed therein. Additionally, a solid may be de-stabilized into an amorphous phase, which may appear as a liquid. Consequently, the terms "liquid" compositions and "flowable" compositions are used interchangeably herein. Most typically, liquids contemplated herein will have a dynamic viscosity of between 500 and 2,500 cP.

Consequently, it should be appreciated that contemplated compositions and methods allow for therapeutic coverage of the entire mycotic nail bed, eradicating the proliferating and non-proliferating spores quickly so that new disease-free nail plate and nail bed below can replace the mycotic tissue (concurrent with linear growth). Due to the relatively high concentration of active agent (preferably terbinafine), a reservoir is created that can spread from the site of deposition proximally through the ridges and caverns of the nail bed. Moreover, due to the hydrophobic nature of the carrier, the active agent is quickly absorbed into the nail plate and so forms an antifungal barrier that may prevent proximal and ventral fungal invasion. It should also be recognized that the hydrophobic nature of the carrier will reduce systemic absorption of the active agent, while at the same to promote partitioning of the active agent into the nail plate. In addition, contemplated formulations have a viscosity that balances fluid distribution in the subungual space with the ability to inject the formulation through small-bore cannulas (e.g., blunt-tip 30-gauge cannula) to so prevent or significantly reduce further lifting of the nail plate (onycholysis). Such cannulas are also blunt enough to allow delivery of the active agent into the center of the mycotic nail bed space without trauma or damage to the nail bed epithelium, and precise enough to allow a physician to treat entry points such as the lateral edge, and into middle of the tough-to-treat fungal mass (dermatophytoma). Viewed from a different perspective, proper viscosity of contemplated formulations will balance numerous requirements for a therapeutic effect: Retention of a liquid composition in the subungual space at therapeutic quantities, while allowing for administration and passive distribution (e.g., via capillary action and/or mechanical force due to toe movement) of the liquid formulation throughout the subungual space without loss due to leakage. Most preferably, such administration is performed using a blunt cannula having a size that prevents trauma.

Therefore, it should be appreciated that contemplated terbinafine (or other antifungal) liquid formulations for treatment of onychomycosis are directed towards flowable liquid forms of terbinafine that can be delivered topically under the nail plate with very high local drug concentrations (and/or where desired also) onto the surface of the nail bed. The concentrated and viscous liquid formulation is preferably delivered through a small-bore cannula and moved to the difficult to reach boundaries of the disease area by substantially filling the subungual space created by the disease. In this context it should be noted that the drug movement is primarily due to action of liquid flow, and less dependent on drug diffusion into the tissues. Drug transport also benefits from the pumping action resulting from cyclical pressure pulses that occur in the nail unit as the patient walks and puts pressure on the toe. The small-bore cannula is also an effective tool of penetrating the debris created by the dermatophyte in the subungual space. Dermatophytoma, a form of mycotic disease giving an undesirable appearance of yellow spikes in the nail, are caused by a polysaccharide matrix formed by the fungus and are known to be difficult to treat due to poor drug penetration. Notably, insertion of the cannula through the disease matrix and depositing liquid drug in a central location of the disease area has been shown to be an effective delivery method.

Significantly, it should be recognized that the local delivery and retention of active antifungal agent (preferably terbinafine) to the disease location is not dependent on systemic absorption of the drug. Indeed, the use of a hydrophobic solvent helps prevent partitioning of the active antifungal agent (preferably terbinafine) into the capillary system of the nail bed. Thus, very high local drug concentrations can be achieved with the topical subungual administration method without the risk of liver toxicity associated with the oral drug administration.

Terbinafine is most commonly provided as a hydrochloride salt, which appears as a crystalline high melting solid. A free-base form of terbinafine is also known, appearing as a lower melting crystalline solid. Liquid forms of terbinafine may be prepared by dissolving the solids in solvents. However, concentrations that can be achieved are limited by solubility, as well as the pharmaceutical acceptability of the solvent used. More useful in achieving high drug concentration is an amorphous form of terbinafine that appears as a liquid at room temperature. An amorphous form of terbinafine may be therefore be prepared by identifying an appropriate crystallization inhibitor designed to prevent formation of the thermodynamically preferred crystalline solid. However, the lower melting free base form is more amenable to stabilizing the substance in the liquid state, and further benefits from the absence of material weight associated with the counter ion that occurs with a salt form.

For example, one especially contemplated liquid pharmaceutical composition will include a pharmaceutically acceptable carrier that comprises a hydrophobic solvent, an optional hydrophilic solvent, a polymeric film-forming agent, and an antifungal agent, wherein the antifungal agent is stabilized or dissolved in the pharmaceutically acceptable carrier and present at a concentration of at least 10 wt %, or at least 20 wt %, or at least 40 wt %, and wherein the pharmaceutical composition has a viscosity of between about 500-2,500 cP (mPa*s). In preferred embodiments, the hydrophobic solvent comprises diisopropyl adipate, isopropyl myristate, isostearic acid, and benzyl alcohol as co-solvents, ethyl cellulose as the polymeric film forming agent, and at least 40 wt % terbinafine as the antifungal agent. As such, the viscosity of the pharmaceutical composition may be approximately between 750-1,500 cP (mPa*s).

With respect to suitable hydrophobic solvents it should be noted, that various solvents, solvent systems, and crystallization inhibitors are also deemed appropriate, and especially contemplated hydrophobic solvents and co-solvents include benzyl alcohol, isostearic acid, isostearyl alcohol, cinnamyl alcohol, benzyl benzoate, diisopropyl adipate, diethyl sebacate, and/or isopropyl myristate. Still further contemplated hydrophobic solvents include various alkanes, alkanols, dialkylethers, cycloalkanes, various saturated and unsaturated fatty acids (including oleic acid, linoleic acid), esters (oleyl oleate), monoglycerides (glyceryl monooleate), diglycerides, triglycerides, natural and synthetic oils (sesame oil, soybean oil, peanut oil, corn oil, olive oil, vegetable oil, etc.), etc. For example, alternative solvents and co-solvents include hexane, cyclohexane, benzene, toluene, diethylether, 1,4-dioxane, castor oil, etc. In further contemplated embodiments, and especially where a hydrophilic solvent having miscibility with the hydrophobic solvent(s) is used, such hydrophilic solvent can be included in the carrier. Especially contemplated hydrophilic solvents with dual miscibility in hydrophobic and hydrophilic phases include 2-pyrrolidone, N-methylpyrrolidone, dimethyl isosorbide, propylene carbonate, and D,L-lactic acid. In further contemplated aspects it is noted that terbinafine free base is also soluble in a solution of a dissolved solid or liquid acid in a solvent. Inorganic acids include phosphoric, and hydrochloric acids, and organic acids include D- and/or L-lactic, malic, maleic, malonic, fumaric, tartaric, succinic, citric, acetic, ascorbic, and propionic acids. The solvents to dissolve the acid include ethanol, isopropanol, acetone, benzyl alcohol, and acetophenone.

In this regard, it must be appreciated that preferred solvents, solvent systems, and crystallization inhibitors (e.g., those having at least two solvents as a solvent or inhibitor mixture, typically in a single phase mixture) will solubilize or prevent precipitation of the active agent, and especially terbinafine salt or terbinafine free base, at a concentration of at least 15 wt %, or at least 20 wt %, or at least 25 wt %, or at least 30 wt %, or at least 35 wt %, or at least 40 wt %, or at least 45 wt %. For example, suitable active agent (e.g., terbinafine) concentrations in the hydrophobic solvent will be 10-15 wt %, or 15-20 wt %, or 20-25 wt %, or 25-30 wt %, or 30-35 wt %, or 35-40 wt %, or 40-45 wt %, or 45-50 wt %, or even higher. Thus, terbinafine concentrations may be 15-30 wt %, or 25-40 wt %, and especially 40 wt %, or 41 wt %, or 42 wt %, or 43 wt %, or 44 wt %, or 45 wt %.

Moreover, thusly solubilized or liquefied active agent will preferably remain stable (i.e., will not precipitate) in a flowable physical form over extended periods of time, including at least 1 week, at least 2 weeks, at least 4 weeks, at least 8 weeks, or at least 12 weeks, or at least 6 months, or at least 1 year when the composition is stored at 25° C. and 60% relative humidity. Most preferably, the antifungal agent will be stable at the employed concentrations, even when stored at reduced temperatures (e.g., 4-5° C.) over extended periods of time (e.g., at least 1 week, at least 2 weeks, at least 4 weeks, at least 8 weeks, or at least 12 weeks, or at least 6 months, or at least 1 year).

With respect to terbinafine it is also contemplated that terbinafine is most commonly provided as a hydrochloride salt, which appears as a crystalline high melting solid. The free base form of terbinafine is also known, appearing as a lower melting crystalline solid. Liquid forms of terbinafine may be prepared by dissolving the solids in solvents. However, concentrations that can be achieved are limited by solubility, as well as the pharmaceutical acceptability of the solvent used. More useful in achieving high drug concentration is an amorphous form of terbinafine that appears as a liquid at room temperature. An amorphous form of terbinafine may be prepared by identifying an appropriate crystallization inhibitor designed to prevent formation of the thermodynamically preferred crystalline solid. The lower melting free base form is more amenable to stabilizing the substance in the liquid state, and further benefits from absence of material weight associated with the counterion that occurs with a salt form. Viewed from a different perspective, terbinafine formulations can be prepared in which terbinafine is present in a supersaturated form without precipitation or crystallization.

Of course, it should be appreciated that while terbinafine is a particularly preferred antifungal agent, various other antifungal or therapeutic agents are also deemed appropriate for use herein, and especially contemplated alternative antifungal agents include various allylamine antifungal drugs (e.g., naftifine, tolnaftate), morpholine antifungal drugs (e.g., amorolfine), polyene antifungal drugs (e.g., amphotericin B, nystatin, natamycin, rimocidin, candicin), and/or an azole antifungal drugs (e.g., clotrimazole, miconazole, ketoconazole, itraconazole, fluconazole). Most typically, the drug concentration of such compounds in contemplated liquid pharmaceutical composition will be at least 10 wt %, more typically at least at least 15 wt %, or at least 20 wt %, at least 25 wt %, at least 30 wt %, at least 35 wt %, at least 40 wt %, and even higher. For example, concentrations of the contemplated alternative antifungal agents in the hydrophobic solvent will be 5-10 wt %, or 10-15 wt %, or 15-20 wt %, or 20-25 wt %, or 25-30 wt %, or 30-35 wt %, or 35-40 wt %, or 40-45 wt %, or 45-50 wt %, or even higher. Thus, terbinafine concentrations may be 15-30 wt %, or 25-40 wt %, and especially 40 wt %, or 41 wt %, or 42 wt %, or 43 wt %, or 44 wt %, or 45 wt %.

Advantageously, even at such high concentrations, systemic absorption is typically reduced or entirely avoided due to the hydrophobic nature of the liquid pharmaceutical composition. Therefore, adverse systemic and/or hepatic effects are substantially eliminated. Moreover, with such high concentrations of terbinafine and other alternative agents, the fungicidal effect is pronounced, and even effective against spore forms of the nail fungus. Indeed, it has been shown that multiples of the required MIC for spore killing in the nail plate and nail bed can be achieved using contemplated formulations.

Suitable polymeric film forming agents especially include linear polymeric film forming agents, which may have a polymeric or co-polymeric backbone. For example, suitable linear polymeric film forming agents may be based on a carbohydrate or polyethylene backbone with appropriate substituents, or on a polyvinyl pyrrolidone backbone. Likewise, suitable film forming agents also include various acrylates, acrylamides, etc. Most preferably, the polymeric film forming agent will be soluble in the hydrophobic solvent and as such will also be a hydrophobic film forming agent. Moreover, the film forming agents can also interfere with the physical stability of the active agent (e.g., prevent precipitation or crystallization of the active agent), thereby providing a homogeneous flowable physical form at all contemplated storage temperatures, including refrigerated temperatures. Therefore, contemplated film forming agents include alkyl cellulose (and particularly ethyl cellulose), hydroxyalkyl cellulose (and especially hydroxypropyl cellulose), various forms of carbomer (cross linked acrylic acid) and glycols, etc. Viewed from a different perspective, preferred film forming agents especially include low polarity film forming agents that will dissolve in the hydrophobic carrier at the concentration required to achieve the desired viscosity. Alternative film forming agents may include triethyl citrate, triacetin, trimethyl citrate, triethyl citrate, tributyl citrate, diethyl phthalate, dibutyl phthalate, ethyl lactate, fatty acids (lauric acid, stearic acid, isostearic acid, capric acid, caprylic acid), fatty acid esters (glyceryl mono- or di-stearate, glyceryl monooleate), alkyl alcohols (stearyl alcohol, cetostearyl alcohol) and ethers (cetostearyl ether).

In especially preferred aspects, the hydrophobic solvent(s) and the film forming agent will be compounded such that the resulting liquid pharmaceutical composition will have a viscosity that allows subungual administration via a small-bore cannula, typically at least 25 gauge, more preferably 27 gauge, and even more preferably 30 gauge (or even smaller). Moreover, the viscosity should also be sufficiently high to allow for retention of the administered volume within the subungual space such that at least 50%, or at least 60%, or at least 70%, or at least 80%, or at least 90%, or at least 95% of the administered volume of the liquid pharmaceutical composition will remain in the subungual space without being drained and/or expelled upon ordinary daily activity. Moreover, preferred film forming agents will also promote distribution of the formulation throughout substantially the entire subungual space, typically by capillary action, wicking, and/or surface tension. In still further contemplated aspects, the film forming agent will also promote penetration of the formulation trough the polysaccharidic matrix located between a nail bed and a nail plate of a dermatophytoma. Advantageously, such penetration allows treatment of areas previously deemed untreatable.

Therefore, in some embodiments the film forming agent will be added to the formulation in an amount that produces suitable viscosities for administration via a cannula and retention in the subungual space. For example, contemplated viscosities will be between 500-700 cP (mPa*s), or between 700-900 cP (mPa*s), or between 800-1,200 cP (mPa*s), or between 1,000-1,500 cP (mPa*s), or between 1,200-1,800 cP (mPa*s), or between 1,500-2,000 cP (mPa*s), or between 1,800-2,200 cP (mPa*s), or between 2,000-5,500 cP (mPa*s), or between 2,500-4,000 cP (mPa*s), and in some cases even higher. Thus, contemplated viscosities will typically be less than 3,000 cP, or less than 2,500 cP, or less than 2,000 cP, or less than 1,800 cP, or less than 1,500 cP, or less than 1,000 cP. In other embodiments, contemplated viscosities will be at least 500 cP, or at least 600 cP, or at least 700 cP, or at least 800 cP, or at least 900 cP, or at least 1,000 cP.

Most notably, it should therefore be recognized that the combination of hydrophobic solvent(s) and polymeric film forming agent will facilitate during and after administration to the subungual space lateral, proximal, and distal mobility within the subungual space while retaining the liquid pharmaceutical composition within the subungual space. Moreover, due to the specific composition, the liquid pharmaceutical composition will also penetrate into and through the polysaccharide matrix that is often associated with the fungal infection. Therefore, administration of the contemplated formulations need not necessarily be up to the leading edge of the diseased area, but may be to a location that is somewhat removed from the edge (e.g., at least 1 mm away, or at least 2 mm away, or at least 3 mm away, or at least 5 mm away).

In addition, upon suitable choice of solvents it must also be recognized that the concentration of active pharmaceutical agents can be selected at a sufficiently high level such that the MIC can be achieved not only in the subungual space but also throughout a treatment space adjacent and extending from the infected are in the subungual space. Indeed, due to the hydrophobic nature of the liquid pharmaceutical composition, the active ingredient (and especially terbinafine) will be able to diffuse into the nail plate and nail bed and thus be present in the nail plate and/or nail bed at therapeutically effective concentrations (e.g., at least 1×MIC, or at least 2×MIC, or at least 5×MIC, or at least 10×MIC). Thus, it should be appreciated that a therapeutic effect (e.g., killing of fungus, and in many cases even killing of spores) is achieved not only in the subungual space, but also a significantly larger treatment space. Thus, it is contemplated that the treatment space is at least 105%, or at least 110%, or at least 115%, or at least 120%, or at least 125%, or at least 130%, of the subungual space, or even more. Moreover, it should be appreciated that due to the very high concentration of terbinafine in contemplated formulations and use of hydrophobic solvent in such formulations (allowing terbinafine to preferentially partition into the nail plate rather than systemic circulation), the MIC for antifungal effect can be sustained in the subungual space and the treatment space over a period of at least 1-3 days, or at least 3-7 days, or at least 14 days, or at least 30 days, or at least 60 days, or at least 90 days, or even longer.

Thus, and viewed from a different perspective, terbinafine concentrations in the subungual and/or treatment space can be maintained at or above MIC over a period of at least 7 days, or at least 14 days, or at least 30 days upon single administration of a liquid formulation in a volume of no more 100 µL, or a volume of no more 90 µL, or a volume of no more 80 µL, or a volume of no more 70 µL, or a volume of no more 50 µL, or a volume of no more 40 µL, or a volume of no more 30 µL, or a volume of no more 20 µL, or a volume of no more 10 µL.

Among other things, the increased therapeutic effect is thought to be produced by the high concentration of the antifungal agent (e.g., terbinafine), the motility and retention of the antifungal agent (e.g., terbinafine) in the subungual space at high concentrations, and the diffusion of the antifungal agent (e.g., terbinafine) from the hydrophobic solvent into the nail plate to achieve therapeutically effective concentrations in the nail plate. As the nail plate advances distally during nail growth, the antifungal agent (e.g., terbinafine) diffused and retained in the nail plate will present an effective barrier to fungal growth and re-establishment, and a healthy nail plate will ultimately have replaced diseased nail plate via growth.

As will be readily appreciated, contemplated pharmaceutically acceptable carriers may include additional agents such as antioxidants and/or diluents, and optionally further non-functional agents that may help visualization such as pigments, dyes, and fluorescent agents. Where desirable, stabilizers counteracting precipitation or crystallization may be included, however, it should be appreciated that in some embodiments the antifungal agent (e.g., terbinafine) will be stable in a flowable physical form at very high concentrations for at least 4 weeks, or at least 8 weeks, or at least 12 weeks, or at least 6 months, or at least 9 months, or at least 12 months when stored at standard conditions (25° C. and 60% relative humidity). Moreover, where dormant spore eradication is desired, additional agents such as ciclopirox olamine can be added to contemplated formulations.

Therefore, and viewed form a different perspective, an embodiment of the inventive subject matter is directed to high-dose antifungal liquid pharmaceutical compositions that include a pharmaceutically acceptable carrier comprising a hydrophobic solvent, an optional hydrophilic solvent, an optional polymeric film forming agent, and an antifungal agent at a concentration of at least 20 wt %, or at least 25 wt %, at least 30 wt %, or at least 35 wt %, or at least 40 wt % of the composition. Most typically, the antifungal agent is made to remain in a flow-able physical form in the pharmaceutically acceptable carrier and is stable for at least 4 weeks when the composition is stored at 25° C. and 60% relative humidity, and the pharmaceutical composition has a viscosity of between about 500-2,500 cP (mPa*s). As noted before, it should be appreciated that the stability of such formulations may extend beyond 4 weeks, and typical stability periods include at least 8 weeks, at least 12 weeks, at least 6 months, at least 9 months, and at least 1 year, and even longer when the composition is stored at 25° C. and 60% relative humidity. With respect to the hydrophobic solvent, the hydrophilic solvent, the polymeric film forming agent, and the antifungal agent, the same considerations as noted above apply.

Moreover, it should be noted that the formulations presented herein will generally be suitable as a vehicle for subungual administration of any agent where the formulation is desired to be retained in the subungual space for an extended period of time. Most typically at least 50%, or at least 60%, or at least 70%, or at least 80%, or at least 90%, or at least 92%, or at least 95% of the formulation is retained over a period of at least 1 day, or at least 3 days, or at least 1 week, or at least 2 weeks, or at least 3 weeks, or at least 4 weeks, or at least 2 months or even longer.

In view of the above, it should therefore be recognized that contemplated uses especially include various methods of subungual administration in a mammal. In such methods, it is typically contemplated that the liquid pharmaceutical compositions presented herein are subungually administered to a space that is located between the nail plate and the nail bed, typically via direct administration from a cannula that is inserted through or beyond the hyponychium into the subungual space. In this context, it should also be recognized that the administration of the liquid pharmaceutical composition does not require initial direct contact with the affected zone or border of infection as the liquid composition is flowable and can passively move to the affected zone (e.g., by compression and pressure relief during ordinary daily activity). Typically, administration through a cannula will require insertion of the cannula through the hyponychium and advancement of the cannula into the subungual space between the nail plate and the nail bed. Most preferably, the cannula is a blunt-tip cannula (e.g., 25-gauge, 28-gauge, 30-gauge) with one or two lateral openings in a distal portion of the cannula. Moreover, it is also preferred that the liquid pharmaceutical composition is administered to fill at least 50%, or at least 60%, or at least 70%, or at least 80%, or at least 90%, or at least 95% of the void space between the nail bed and the nail plate. Where desired, administration may also include topical administration in the lateral nail fold. Administration may also be performed in the open space between the nail bed and nail plate where fungal presence is abundant.

As the formulation is administered as a liquid that can advance to areas of the subungual space not directly accessible by the cannula, administration to the subungual space can be performed atraumatically (i.e., will not lead to bleeding and/or nail plate lifting or nail plate/nail bed separation). Consequently, treatment comfort and adherence is significantly improved and does not require us of anesthetic agents.

Therefore, contemplated methods will be particularly suitable for treatment of onychomycosis in which a liquid pharmaceutical composition is subungually administered. Most typically, the liquid pharmaceutical composition comprises a pharmaceutically acceptable carrier that includes a hydrophobic solvent, an optional hydrophilic solvent, a polymeric film forming agent, and an antifungal agent, and the antifungal agent is made to remain in a flow-able physical form in the pharmaceutically acceptable carrier and present at a concentration of at least 10 wt % (e.g., at least 20%, or at least 30%, or at least 40%). As noted above it is further generally preferred that the pharmaceutical composition has a viscosity of between about 500-2,500 cP (mPa*s). Likewise, in view of the enhanced penetration into and through the polysaccharide matrix, the inventors also contemplate a method of treating a dermatophytoma (which was heretofore deemed difficult to treat or untreatable without removal of the nail) in which a liquid pharmaceutical composition is subungually administered into a polysaccharide matrix located between a nail bed and a nail plate without removing the nail plate. Most typically, the antifungal agent is made to remain in a flow-able physical form in the pharmaceutically acceptable carrier and present at a concentration of at least 20 wt %, and the pharmaceutical composition has a viscosity of between about 500-2,500 cP (mPa*s). With respect to suitable liquid pharmaceutical compositions, the same considerations as noted above apply.

Viewed from another perspective, the inventors also contemplate a method of retaining a liquid pharmaceutical composition that includes an antifungal agent in a subungual space. In this context, it is critical to appreciate that it is not only the administration of the pharmaceutical composition, but also the effective penetration to the affected area and retention in the affected area (and ideally retention in the nail plate) that increases treatment success. In such methods, the liquid pharmaceutical composition is subungually administered into the subungual space, wherein the liquid pharmaceutical composition is as described above. Advantageously, due to the hydrophobic nature of the formulation, passive wash out (e.g., due to shower or bathing) is also significantly reduced. Where terbinafine free base is employed, such advantage is further increased.

Upon administration, it is typically contemplated that at least 60%, or at least 70%, or at least 80%, or at least 85%, or at least 90%, or at least 90% of the administered volume is retained within the subungual space. Most typically, retention is over a period of at least 6 hours, or at least 12 hours, or at least 24 hours, or at least 2 days or at least 7 days. Thus, very high concentration of the antifungal agent are locally administered and retained within a treatment space, which will advantageously maintain antifungal agent concentrations well above the MIC as noted above. For example, absorption into the local tissue (nail bed and nail plate) provides significant and therapeutic drug concentration for at least 1 month, or at least 2 months, or at least three months, and even longer.

As contemplated formulations have the ability to migrate within the subungual space and diffuse into a larger treatment area, the inventors also contemplate a method of treating onychomycosis in which liquid pharmaceutical compositions as presented herein are subungually administered to a location that does not contact the visible proximal edge of an area affected by onychomycosis. The liquid pharmaceutical composition is then allowed to passively migrate from the location to at least the visible proximal edge of the area affected by onychomycosis, typically via compression/decompression of the treatment area during walking. For example, the location may be at least 1 mm, or at least 2 mm, or at least 3 mm, or at least 5 mm away from the visible proximal edge of the area affected by onychomycosis. It should be pointed out that such passive migration is not the same as diffusion. Nevertheless, diffusion of the antifungal agent from the liquid pharmaceutical composition into the nail bed and especially into the nail plate is also especially contemplated. Thus, a stable and flowable liquid form of terbinafine containing excipients that promote secondary diffusion into the nail plate to create a depot of local antifungal drug concentration are particularly desirable.

Moreover, as the compositions presented herein will typically have a high antifungal drug concentration, the liquid pharmaceutical compositions will act as a drug delivery system that sustains antifungal drug concentration (e.g., at least 1×MIC) for at least 30 days, more preferably at least 60 days, and even more preferably at least 90 days after administration.

Thus, it should be appreciated that a flowable liquid form of terbinafine can be delivered atraumatically and topically in very high local concentration under the nail plate and onto the surface of the nail bed. Delivery of the liquid drug is preferably performed using a small-bore blunt tip cannula that avoids damage to the nail bed/nail plate attachment, as well as other trauma to the nail anatomy. The concentrated and viscous liquid drug is delivered through the cannula and moved to the difficult to reach boundaries of the disease area by substantially filling the subungual volume created by the disease. In this context, it should be noted that drug movement is primarily due to action of liquid flow, and less dependent on drug diffusion through the tissues. Drug transport also benefits from the pumping action resulting from cyclical pressure pulses that occur in the subungual space as the patient walks and puts pressure on the toe. It should also be appreciated that the small-bore cannula is an effective tool of penetrating the debris created by the dermatophyte in the subungual space. Dermatophytoma, a form of mycotic disease giving an undesirable appearance of yellow spikes in the nail, are caused by a polysaccharide matrix formed by the fungus and are known to be difficult to treat due to poor drug penetration. Insertion of the cannula through the disease matrix and depositing liquid drug in a central location of the disease area has been shown to be a more effective delivery method. Significantly, local delivery of terbinafine to the disease location is not dependent on systemic absorption of the drug. Very high local tissue drug concentration can be achieved with the topical subungual delivery method without the liver toxicity associated with the oral drug administration.

EXAMPLES

Formulations:

Based on the above considerations, the inventors prepared various compositions and exemplary formulations are provided in Table 1 below.

The following protocol was used for all cannulations: Inspect the nail unit and provide nail care as needed (filing and sanding of the dorsal nail plate to help ensure optimal visualization of the area of affected nail). Measure the width of the nail plate using a caliper and identify 2 to 4 proposed cannulation paths. Measure the length of affected nail along each of the proposed cannulation paths and determine the target depth of cannulation for each cannulation path (the target insertion depth is 50% of the affected nail length). Cleanse the hyponychium with isopropyl alcohol or povidone iodine and allow to dry and mark the target depth on the 30-gauge cannula. Insert the cannula along the proposed cannulation path. 1 marked cannula will be used for each proposed cannulation path. Advance the 30-gauge cannula until the tip of the cannula is at the mid-depth point of the proposed cannulation path. If the cannulation was atraumatic and painless, the cannula may be advanced up to 3 additional millimeters. If possible, mark the location of the free nail edge immediately above the cannula. Withdraw the cannula and place the withdrawn cannula on the surface of

TABLE 1

| Component | Function | Wt % Composition | | | | | | | | | |
| --- | --- | --- | --- | --- | --- | --- | --- | --- | --- | --- | --- |
| | | F1 | F2 | F3 | F4 | F5 | F6 | F7 | F8 | F9 | F10 |
| Terbinafine free base | Active ingredient | 50.00 | 50.00 | 50.00 | 50.00 | 50.00 | 49.40 | 42.00 | 42.00 | 42.00 | 42.00 |
| Butylated hydroxytoluene | Antioxidant | 0.10 | 0.10 | | 0.10 | 0.10 | 0.10 | 0.20 | 0.20 | 0.20 | 0.20 |
| Benzyl alcohol | Solvent | 2.50 | 2.50 | 0.10 | 2.50 | 2.50 | 2.50 | 2.70 | 2.70 | | |
| Benzyl benzoate | Solvent | | | 49.90 | | | | | | | |
| Diisopropyl adipate | Co-solvent | | 20.00 | | 20.00 | 20.00 | 20.00 | 20.00 | 20.00 | | |
| Diethyl sebacate | Co-solvent | 22.50 | 24.00 | | 24.00 | 24.00 | 24.00 | | | | |
| Isopropyl myristate | Co-solvent | | 3.40 | | | | | 31.10 | 32.10 | 5.80 | 7.80 |
| Isostearic acid | Solvent, Diluent | 24.90 | | | 3.40 | | | | | 25.00 | 22.00 |
| Isostearyl alcohol | Diluent | | | | | 2.50 | | | | | |
| Dimethyl isosorbide | Solvent | | | | | | | | | 15.00 | 15.00 |
| Propylene carbonate | Solvent | | | | | | | | | 5.00 | 5.00 |
| D,L-Lactic acid | Solvent | | | | | | | | | 7.00 | 7.00 |
| Ethanol | Gelling vehicle, solvent | | | | | | 0.70 | | | | |
| Hydroxypropyl cellulose | Gel agent, viscosity increase, film former | | | | | | 0.20 | | | | |
| Ethyl cellulose | Gel agent, viscosity increase, film former | | | | | | | 4.00 | 4.00 | 3.00 | 1.00 |
| Stability | | no | no | no | no | no | no | yes | yes | yes | yes |

Most notably, very high concentrations of terbinafine could be achieved in a hydrophobic carrier. However, stability at standard conditions (at 25° C. and 60% relative humidity, 9 months storage) was shown only for formulations F7 and F8, whereas formulations F1-F6 ultimately precipitated.

Administration:

To ascertain whether or not contemplated formulations can be delivered to the subungual space, the inventors tested access with a 30 gauge blunt cannula (e.g., TSK STERi-GLIDE™ Aesthetic Cannula) in several subjects confirmed with onychomycosis. FIG. 1 depicts an exemplary toe nail with onychomycosis with disease margins marked in black.

the nail plate and photograph. Record the following information for each proposed cannulation path: Length of visualized onychomycosis; Target depth of cannulation; Actual depth of cannulation; Ease of cannulation; Participant complaint of discomfort; and Note any observed bleeding. Following completion of the procedure place a loose-fitting dressing or bandage of the insertion areas. If the second great toe and/or any lesser toe has greater than 4 mm of affected nail (2 mm in case of lesser toe), these nails may be evaluated as well. The cannulation procedure will be followed for all cannulations. The subjects and results for the test population are shown in Tables 2 and 3 below.

TABLE 2

| Subject ID No. | Toe | Nail Length | Nail Thickness | Length of Involvement | Estimated Nail Involvement | Infection Zone Contiguous | If Non Contiguous, # of Zones | Are Non Contiguous Zones Accessible at Free Edge | Dermatophytoma present? | Dermatophytoma Contiguous with Infection Zone | Estimated Area of Involvement | Grade |
|---|---|---|---|---|---|---|---|---|---|---|---|---|
| 901-001 | Right Hallux | 13.0 | 1 | 5.0 | 40% | No | 2 | Yes | No | N/A | 85 | Grade 3 |
| 901-002 | Right Hallux | 14.2 | 1 | 5.0 | 25% | Yes | | N/A | No | N/A | 73 | Grade 3 |
| 901-003 | Right Hallux | 15.7 | 1 | 7.1 | 45% | Yes | | N/A | No | N/A | 100 | Grade 4 |
| 901-004 | Left Hallux | 17.9 | 2 | 4.2 | 28% | Yes | | N/A | No | N/A | 79 | Grade 3 |
| 901-005 | Left Hallux | 16.0 | 2 | 11.9 | 75% | Yes | | N/A | No | N/A | 149 | Grade 5 |
| 901-005 | L2 | 7.2 | 2 | 4.1 | 50% | Yes | | N/A | No | N/A | 26 | Grade 4 |
| 901-006 | Left Hallux | 15.4 | 2 | 8.2 | 40% | Yes | | N/A | No | N/A | 97 | Grade 3 |
| 901-007 | Left Hallux | 16.2 | 1 | 5.6 | 25% | No | 2 | Yes | No | N/A | 74 | Grade 3 |
| 901-007 | Right Hallux | 14.9 | 1 | 8.2 | 25% | Yes | | N/A | No | N/A | 65 | Grade 3 |
| 901-008 | Left Hallux | 11.7 | 1 | 5.3 | 50% | Yes | | N/A | No | N/A | 117 | Grade 4 |
| 901-009 | Right Hallux | 16.3 | 1 | 7.8 | 50% | Yes | | N/A | No | N/A | 86 | Grade 4 |
| 901-010 | Right Hallux | 12.6 | 2 | 6.1 | 38% | Yes | | N/A | No | N/A | 125 | Grade 3 |
| 901-010 | R4 | 7.7 | 1 | 7.7 | 75% | Yes | | N/A | No | N/A | 46 | Grade 5 |
| 901-011 | Right Hallux | 13.7 | 2 | 9.4 | 75% | Yes | | N/A | No | N/A | 85 | Grade 5 |
| 901-011 | R3 | 9.2 | 1 | 4.3 | 50% | Yes | | N/A | No | N/A | 28 | Grade 4 |
| 901-012 | Left Hallux | 18.3 | 1 | 16.8 | 50% | Yes | | N/A | Yes | Yes | 199 | Grade 4 |

TABLE 3

| Subject ID No. | Toe | Cannulation Number | Length of suspected onycholysis | Target cannulation depth | Was target cannulation depth obtained? | Was target cannulation depth exceeded? | Actual cannulation depth | Ease of cannulation | Participant complaint of pain? | Any bleeding observed? | Participant Pain Score |
|---|---|---|---|---|---|---|---|---|---|---|---|
| 901-001 | Right Hallux | #1 | 4.98 | 2.49 | Yes | No | 2.49 | 2 = Very easy | No | No | 0 |
| 901-001 | Right Hallux | #2 | 3.62 | 1.82 | Yes | No | 1.82 | 2 = Very easy | No | No | 0 |
| 901-002 | Right Hallux | #1 | 5 | 2.5 | Yes | Yes | 2.54 | 2 = Very easy | No | No | 0 |
| 901-003 | Right Hallux | #1 | 7.1 | 3.55 | Yes | No | 3.55 | 2 = Very easy | No | No | 0 |
| 901-003 | Right Hallux | #2 | 5.4 | 2.7 | Yes | Yes | 3.55 | 2 = Very easy | No | No | 0 |
| 901-004 | Left Hallux | #1 | 4.2 | 2.1 | Yes | No | 2.1 | 2 = Very easy | No | No | 1 |
| 901-004 | Left Hallux | #2 | 4.4 | 2.3 | Yes | No | 2.3 | 2 = Very easy | No | No | 1 |
| 901-005 | Left Hallux | #1 | 11.9 | 5.95 | Yes | Yes | 6 | 2 = Very easy | No | No | 1 |
| 901-005 | L2 | #1 | 4.1 | 2 | Yes | No | 2 | 2 = Very easy | No | No | 1 |
| 901-006 | Left Hallux | #1 | 8.2 | 4.1 | Yes | No | 4.1 | 2 = Very easy | No | No | 1 |
| 901-006 | Left Hallux | #2 | 5.2 | 2.6 | Yes | No | 2.6 | 2 = Very easy | No | No | 1 |
| 901-006 | Left Hallux | #3 | 6.4 | 3.2 | Yes | No | 3.2 | 2 = Very easy | No | No | 1 |
| 901-007 | Right Hallux | #1 | 8.2 | 4.1 | Yes | No | 4.1 | 2 = Very easy | No | No | 0 |
| 901-007 | Left Hallux | #1 | 5.6 | 2.8 | Yes | No | 2.8 | 2 = Very easy | No | No | 0 |
| 901-007 | Left Hallux | #2 | 3.4 | 1.7 | Yes | Yes | 2.5 | 2 = Very easy | No | No | 0 |
| 901-008 | Left Hallux | #1 | 5.3 | 2.65 | Yes | No | 2.7 | 2 = Very easy | No | No | 0 |
| 901-008 | Left Hallux | #2 | 5.3 | 2.65 | Yes | Yes | 3 | 2 = Very easy | No | No | 0 |
| 901-009 | Right Hallux | #1 | 7.82 | 3.91 | Yes | Yes | 4 | 2 = Very easy | No | No | 0 |
| 901-009 | Right Hallux | #2 | 3.38 | 1.69 | Yes | No | 1.7 | 2 = Very easy | No | No | 0 |
| 901-010 | Right Hallux | #1 | 6.05 | 3.03 | Yes | No | 3 | 2 = Very easy | No | No | 0 |
| 901-010 | Right Hallux | #2 | 5.24 | 2.62 | Yes | No | 2.6 | 2 = Very easy | No | No | 0 |
| 901-010 | R4 | #1 | 7.74 | 3.87 | Yes | Yes | 4 | 2 = Very easy | No | No | 0 |
| 901-011 | Right Hallux | #1 | 9.4 | 4.7 | Yes | No | 4.7 | 2 = Very easy | No | No | 0 |
| 901-011 | Right Hallux | #2 | 4.8 | 2.4 | Yes | No | 2.4 | 2 = Very easy | No | No | 0 |
| 901-011 | R3 | #1 | 4.25 | 2.13 | Yes | Yes | 2.25 | 2 = Very easy | No | No | 0 |
| 901-012 | Left Hallux | #1 | 16.8 | 8.4 | Yes | No | 8.4 | 2 = Very easy | No | No | 0 |
| 901-012 | Left Hallux | #2 | 5.75 | 2.9 | Yes | No | 2.9 | 2 = Very easy | No | No | 0 |
| 901-012 | Left Hallux | #3 | 6.33 | 3.12 | Yes | No | 3.1 | 2 = Very easy | No | No | 0 |

As can be readily seen, 12 subjects had 28 procedures, and all were rated by the Investigator as "Very Easy" with the target length achieved in all cannulations and no bleeding or spontaneous complaints of pain. Patients considered 75% of cannulations painless while the remaining 25% were rated "very mild pain" (Score of 1, on scale of 1-10).

Tissue Concentration:

To establish the significantly increased quantities for terbinafine available to the tissue, the inventors compared tissue concentrations for terbinafine as a function of different modes of administration. Specifically, tissue concentrations were determined for oral administration of terbinafine, subungual administration of terbinafine in a solid pellet (TMI-358) form as described in U.S. Pat. No. 7,135,194, and predicted for subungual administration of terbinafine in a liquid formulation as described herein.

Exemplary results for these treatments are provided in Table 4 and Table 5. More specifically Table 4 provides terbinafine concentrations for all treatment options for the nail bed, the nail plate, and the distal nail, and Table 5 provides numerical comparison between these methods.

TABLE 4

| | | Average Terbinafine Concentration (μg/g) | | |
|---|---|---|---|---|
| | n= | Nail Bed | Nail Plate | Distal Nail |
| Sample Time = 4 Days | | | | |
| (1) TMI-358 distal | 3 | 19.51 | 0.08 | 0.00 |
| (1) TMI-358 subungual | 2 | 778.73 | 304.13 | 12.65 |
| (3) TMI-358 distal | 1 | 15.27 | 0.00 | 0.00 |
| (3) TMI-358 lateral | 2 | 0.80 | 0.09 | 0.31 |
| (3) TMI-358 proximal | 2 | 0.17 | 0.10 | 0.73 |
| Sample Time = 8 Days | | | | |
| Oral × 7 days | 4 | 0.40 | 0.12 | 0.16 |
| Sample Time = 15 Days | | | | |
| (1) TMI-358 distal | 5 | 0.62 | 0.93 | 2.85 |
| (1) TMI-358 subungual | 3 | 5.10 | 2.02 | 30.30 |
| Oral × 14 days | 3 | 3.06 | 0.00 | 0.04 |
| Sample Time = 22 Days | | | | |
| (1) TMI-358 distal | 3 | 0.20 | 0.00 | 0.00 |
| (1) TMI-358 subungual | 3 | 4.59 | 0.58 | 42.42 |
| Sample Time = 29 Days | | | | |
| (1) TMI-358 distal | 3 | 0.34 | 0.88 | 2.81 |
| (1) TMI-358 subungual | 3 | 0.48 | 0.14 | 82.35 |
| Oral × 28 days | 3 | 4.05 | 0.02 | 0.04 |
| Oral × 7 days | 3 | 2.82 | 0.02 | 0.00 |
| Topical × 28 days | 3 | 13.01 | 12.34 | 0.48 |
| Sample Time = 43 Days | | | | |
| (1) TMI-358 distal | 3 | 0.10 | 0.00 | 0.05 |
| (1) TMI-358 subungual | 3 | 0.28 | 2.25 | 2.08 |
| (3) TMI-358 distal | 1 | 3.02 | 0.00 | 0.00 |

TABLE 5

| | | Day | 5 | 15 | 28 | |
|---|---|---|---|---|---|---|
| Oral Actual (Nail Bed) | Conc. (μg/g) | | 0.4 | 3.06 | 4.05 | |

| | | Day | 4 | 15 | 22 | 29 | 43 |
|---|---|---|---|---|---|---|---|
| Subungual TMI-358 Actual (Nail Bed) | Conc. (μg/g) | | 778.73 | 5.10 | 4.59 | 0.48 | 0.28 |

| | volume admin (μL) | Calc. Dose (mg) |
|---|---|---|
| HSG 42% Liquid Projection (predicted, based on TMI-358) | 50 | 19.53 |

| | Day | 4 | 15 | 22 | 29 | 43 |
|---|---|---|---|---|---|---|
| | | 47797 | 313 | 281 | 29 | 17 |
| Comparison to Oral Steady State (multiple of Oral) | | 11802 | 77 | 69 | 7 | 4 |

Figure 2:
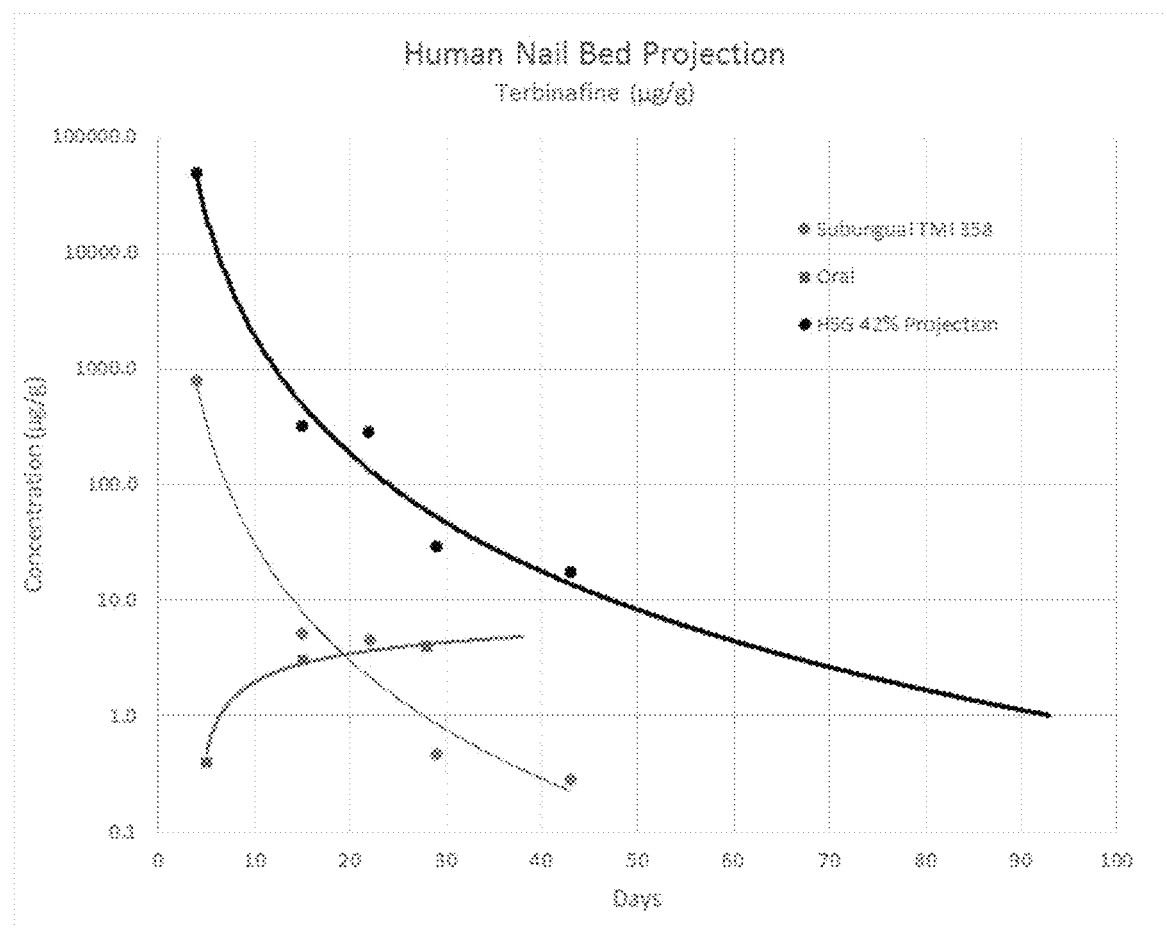
FIG. 2 is a graph depicting terbinafine concentrations as a function of different modes of administration.

FIG. 2 depicts the results in graphical format. As can be readily seen from FIG. 2, the concentration of terbinafine at the nail bed is relatively low where terbinafine was orally administered. Here, terbinafine concentrations increased to a steady-state level due to systemic exposure. In contrast, upon subungual delivery using a solid implant, relatively high terbinafine concentrations were achieved, but significantly decreased over time. On the other hand, where terbinafine was administered and substantially retained in the subungual space and treatment space, very high concentrations were achieved that remained at significantly higher levels as compared to both alternative modes of administration.

Single Dose Pharmacokinetics of Terbinafine Following a Topical (4.2 or 42 mg/kg) Dose in Hanford Miniature Swine: Test article (HSG) is an anti-fungal (49% terbinafine free base) and is a small molecule. The formulation excipients include butylated hydroxytoluene, benzyl alcohol, diisopropyl adipate, diethyl sebacate, and isopropyl myristate. The concentration of terbinafine free base in HSG is 0.49 mg/μL and density is 0.98 g/mL.

Four dose groups of three Hanford Miniature Swine per group, 6 males and six females. One group of two females and one male received a single dose of 4.2 mg/kg terbinafine applied directly to the skin. One group of two males and one female received a single dose of 4.2 mg/kg terbinafine in a Hill Top chamber. One group of two females and one male received a single dose of 42 mg/kg terbinafine applied directly to the skin at ten sites. One group of two males and one female received a single dose of 42 mg/kg terbinafine in ten Hill Top chambers.

As part of a single dose pharmacokinetic study in Hanford Miniature Swine, one group of two females and one male received a single dose of approximately 4.2 mg/kg terbinafine applied directly to the skin. One group of two males and one female received a single dose of approximately 4.2 mg/kg terbinafine in a Hill Top chamber. One group of two females and one male received a single dose of approximately 42 mg/kg terbinafine applied directly to the skin at ten sites. One group of two males and one female received a single dose of approximately 42 mg/kg terbinafine in ten Hill Top chambers. Blood samples were taken from each animal at pre-dose, 1, 2, 4, 6, 8, 12, 24, 48, 72, 96, 120, 144, 168, 192, 216, 240, 288 (Day 12), 336 (Day 14), 384 (Day 16), 432 (Day 18), and 504 (Day 21) hours post dose and plasma terbinafine concentrations were measured for pharmacokinetic analysis. Pharmacokinetic parameters were calculated using calculated, rather than nominal, terbinafine doses using WinNonLin software.

As part of a single dose pharmacokinetic study in Hanford Miniature Swine, one group of two females and one male received a single dose of approximately 4.2 mg/kg terbinafine applied directly to the skin. One group of two males and one female received a single dose of approximately 4.2 mg/kg terbinafine in a Hill Top chamber. One group of two females and one male received a single dose of approximately 42 mg/kg terbinafine applied directly to the skin at ten sites. One group of two males and one female received a single dose of approximately 42 mg/kg terbinafine in ten Hill Top chambers. Blood samples were taken from each animal at pre-dose, 1, 2, 4, 6, 8, 12, 24, 48, 72, 96, 120, 144, 168, 192, 216, 240, 288 (Day 12), 336 (Day 14), 384 (Day 16), 432 (Day 18), and 504 (Day 21) hours post dose and plasma terbinafine concentrations were measured for pharmacokinetic analysis.

Dose Administration: The test article was administered once as a topical dose to a 4 cm2 area on the dorsal surface. The test article is a liquid that was slowly administered with a pipette, using the rounded end of a glass rod to rub the material into the area evenly. Group 1 (low dose) had one area dosed, while Group 2 (high dose) had 10 areas dosed. As the test article (HSG) was running off following dermal dosing, a decision was made to dose 3 animals/group per protocol and the other 3 animals/group using a Hill Top Chamber (25 mm in diameter). Due to the amount of test article it took to wet the webril pad inside of the chamber, the chamber was loaded with 200 µL of the test article.

Blood Sampling: Pharmacokinetic samples were collected on all study animals. At each designated time point, approximately 4 mL of whole blood was collected via temporary jugular catheter or via direct venipuncture of the jugular vein or other appropriate blood vessel. Time tolerance for each collection was consistent with SRC SOPs. Blood samples were placed into blood tubes containing K2EDTA as the anticoagulant. Blood/plasma sample tubes were labeled per SRC SOPs. Samples were gently mixed and placed on ice packs or wet ice pending processing.

Samples were centrifuged at 2000×g, for about 15 minutes, at about 4° C. Plasma samples were then aliquoted into a pre-labeled primary (at least 0.5 mL) and back-up cryovial and temporarily stored frozen on dry ice until storage at about −70° C. Samples were shipped on dry ice to a suitable bioanalytical laboratory (KCAS).

Analytical Methods: Sample analysis involved the extraction of terbinafine and the added terbinafine-d7 (IS) from matrix using liquid-liquid extraction. After extraction, the residue was then subjected to reverse phase high performance liquid chromatography on a Pursuit C18 column and detection of the analytes by tandem mass spectroscopy using the Sciex API5000 LC-MS/MS. This method was previously validated over the range of 0.0200 to 2.00 ng/mL.

Pharmacokinetic Evaluation: Pharmacokinetic calculations were performed using WinNonlin Professional software (Version 4.0.1, Pharsight, Mountain View Calif.). Concentration-time data was analyzed using noncompartmental methods (area/moment analysis). The peak concentration (Cmax) and time of Cmax (Tmax) were taken directly from the observed data. Terbinafine plasma concentrations that were below the quantitation limit of the analytical method (<0.0200) were treated as zero. For this analysis, WinNonlin software chose the data points to include in the calculation of $\lambda z$. WinNonlin software repeats the regression with the last three non-zero concentrations, then the last four, last five, etc. For each regression, an adjusted $R^2$ is computed.

$$\text{Adjusted } R^2 = 1 - \frac{(1-R^2)*(n-1)}{(n-2)}$$

WinNonlin estimates $\lambda z$ using the regression with the largest adjusted $R^2$. If the adjusted $R^2$ does not improve, but is within 0.0001 of the largest $R^2$ value, the regression with the larger number of points is used. The area under the concentration-time curve (AUC) was estimated using the linear trapezoidal with linear interpolation method.

Statistical Analysis: Except for calculation of descriptive statistics, statistical analyses were not performed. All calculations were performed before rounding of data. Therefore, recalculation of descriptive statistics and pharmacokinetic parameter values using rounded values from the tables in this report may yield rounding differences.

Figure 3:
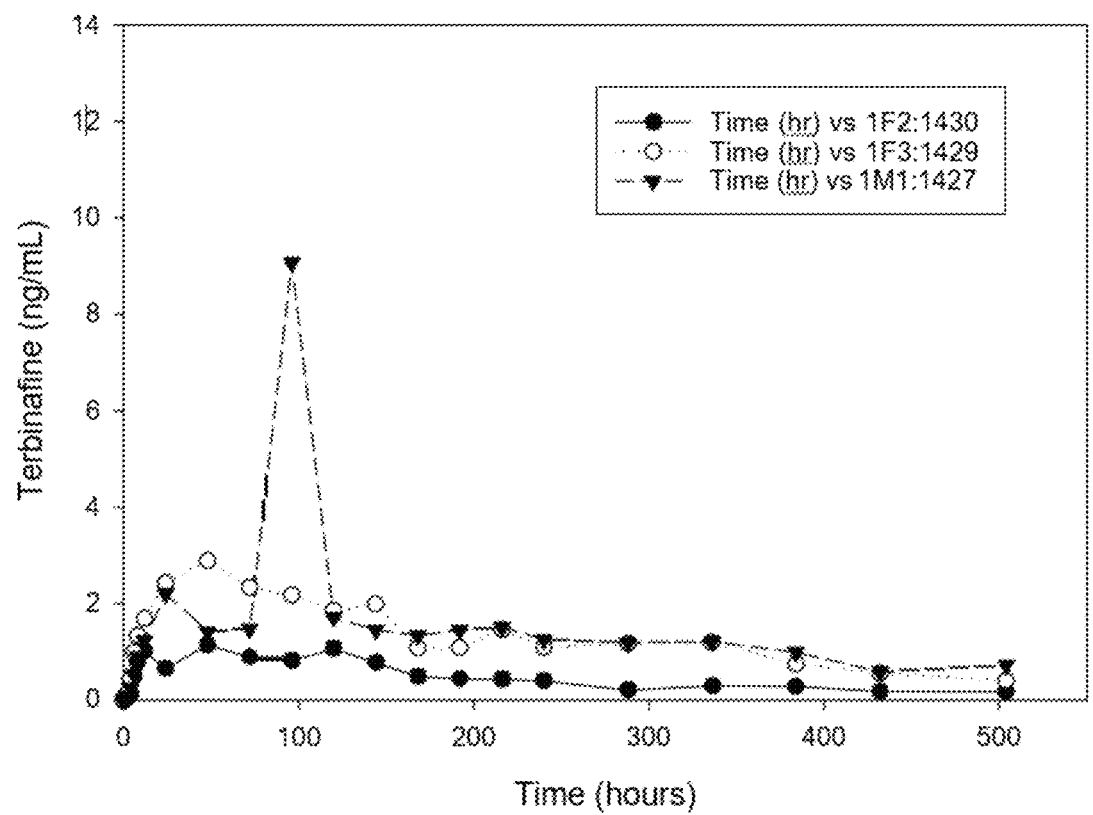
FIG. 3 is a graph depicting terbinafine plasma concentrations versus time after a single topical dose of approximately 4.2 mg/kg Terbinafine applied directly to the skin to Hanford Miniature Swine.

Concentration-Time Profiles: The terbinafine plasma concentration-time profile for a single topical dose (one application site) of approximately 4.2 mg/kg terbinafine for two females and one male is presented in Table 6 below. A graph of the time versus terbinafine plasma concentrations is presented in FIG. 3.

TABLE 6

| | Animal # | | | | |
|---|---|---|---|---|---|
| Time (hr) | 1F2: 1430 | 1F3: 1429 | 1M1: 1427 | Mean | SD |
| 0 | <0.0200 | <0.0200 | <0.0200 | 0 | 0 |
| 1 | 0.0202 | 0.0365 | 0.0317 | 0.029 | 0.007 |
| 2 | 0.0451 | 0.117 | 0.0764 | 0.080 | 0.029 |
| 4 | 0.117 | 0.444 | 0.249 | 0.270 | 0.134 |
| 6 | 0.480 | 0.988 | 0.533 | 0.667 | 0.228 |
| 8 | 0.800 | 1.34 | 0.893 | 1.01 | 0.236 |
| 12 | 1.02 | 1.70 | 1.23 | 1.32 | 0.284 |
| 24 | 0.660 | 2.43 | 2.21 | 1.77 | 0.788 |
| 48 | 1.14 | 2.89 | 1.42 | 1.82 | 0.768 |
| 72 | 0.892 | 2.33 | 1.48 | 1.57 | 0.590 |
| 96 | 0.820 | 2.18 | 9.07 | 4.02 | 3.611 |
| 120 | 1.06 | 1.85 | 1.71 | 1.54 | 0.344 |
| 144 | 0.774 | 1.99 | 1.45 | 1.40 | 0.497 |
| 168 | 0.487 | 1.08 | 1.34 | 0.97 | 0.357 |
| 192 | 0.438 | 1.09 | 1.45 | 0.99 | 0.419 |
| 216 | 0.432 | 1.46 | 1.51 | 1.13 | 0.497 |
| 240 | 0.396 | 1.09 | 1.26 | 0.915 | 0.374 |
| 288 | 0.208 | 1.17 | 1.19 | 0.856 | 0.458 |
| 336 | 0.295 | 1.20 | 1.21 | 0.902 | 0.429 |
| 384 | 0.282 | 0.750 | 0.991 | 0.674 | 0.294 |
| 432 | 0.178 | 0.556 | 0.585 | 0.440 | 0.185 |
| 504 | 0.173 | 0.405 | 0.725 | 0.434 | 0.226 |

Figure 4:
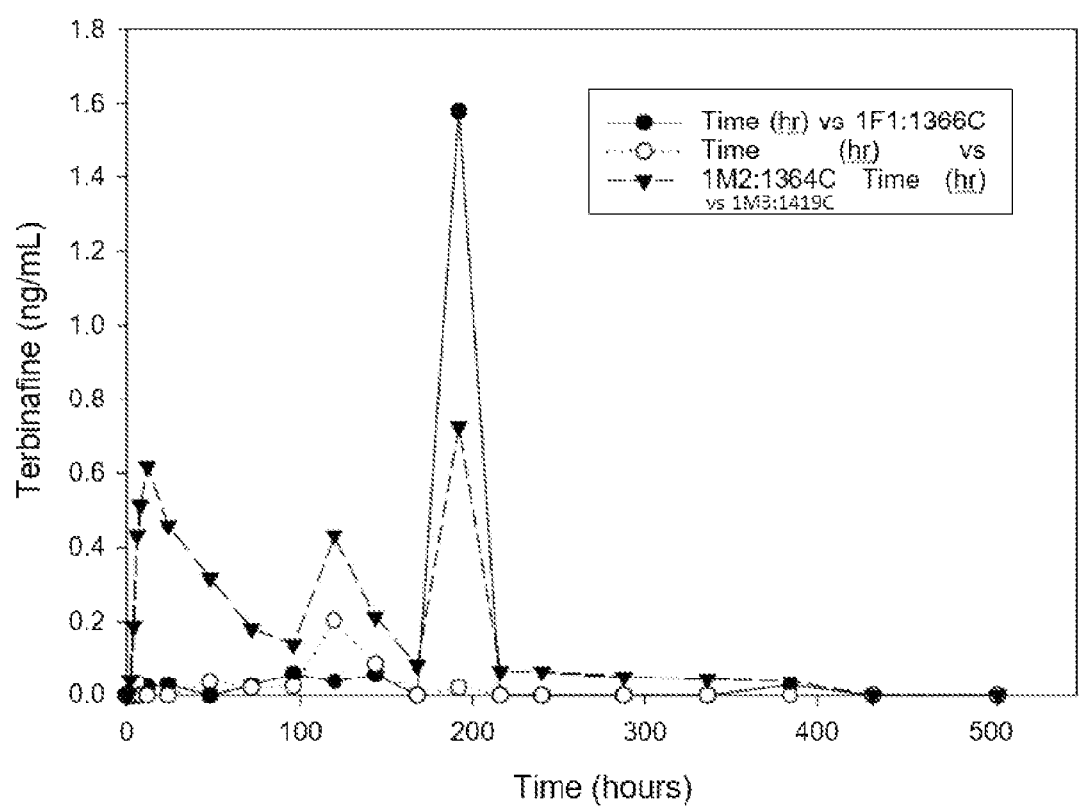
FIG. 4 is a graph depicting terbinafine plasma concentrations versus time after a single topical dose of approximately 4.2 mg/kg Terbinafine applied in a Hill Top Chamber to Hanford Miniature Swine.

The terbinafine plasma concentration-time profile for a single topical dose (one application site) of approximately 4.2 mg/kg terbinafine in Hill Top chambers for one female and two males is presented in Table 7 below. A graph of the time versus terbinafine plasma concentrations is presented in FIG. 4.

TABLE 7

| | Animal # | | | | |
|---|---|---|---|---|---|
| Time (hr) | 1F1: 1366 | 1M2: 1364 | 1M3: 1419 | Mean | SD |
| 0 | <0.0200 | <0.0200 | <0.0200 | 0 | NC |
| 1 | <0.0200 | <0.0200 | <0.0200 | 0 | NC |
| 2 | <0.0200 | <0.0200 | 0.0416 | 0.0416 | NC |
| 4 | <0.0200 | <0.0200 | 0.189 | 0.189 | NC |
| 6 | <0.0200 | 0.0344 | 0.434 | 0.234 | NC |
| 8 | <0.0200 | <0.0200 | 0.514 | 0.514 | NC |
| 12 | 0.0226 | <0.0200 | 0.618 | 0.320 | NC |
| 24 | 0.0304 | <0.0200 | 0.459 | 0.245 | NC |
| 48 | <0.0200 | 0.0394 | 0.318 | 0.179 | NC |
| 72 | 0.0265 | 0.0210 | 0.183 | 0.0768 | 0.0751 |
| 96 | 0.0603 | 0.0254 | 0.140 | 0.0752 | 0.0480 |
| 120 | 0.0389 | 0.205 | 0.432 | 0.225 | 0.161 |
| 144 | 0.0583 | 0.0865 | 0.214 | 0.120 | 0.0677 |
| 168 | <0.0200 | <0.0200 | 0.0842 | 0.0842 | NC |
| 192 | 1.58 | 0.0213 | 0.725 | 0.775 | 0.637 |
| 216 | <0.0200 | <0.0200 | 0.0670 | 0.0670 | NC |
| 240 | <0.0200 | <0.0200 | 0.0662 | 0.0662 | NC |
| 288 | <0.0200 | <0.0200 | 0.0511 | 0.0511 | NC |
| 336 | <0.0200 | <0.0200 | 0.0453 | 0.0453 | NC |
| 384 | 0.0288 | <0.0200 | 0.0390 | 0.0339 | NC |
| 432 | <0.0200 | <0.0200 | <0.0200 | 0 | NC |
| 504 | <0.0200 | <0.0200 | <0.0200 | 0 | NC |

Figure 5:
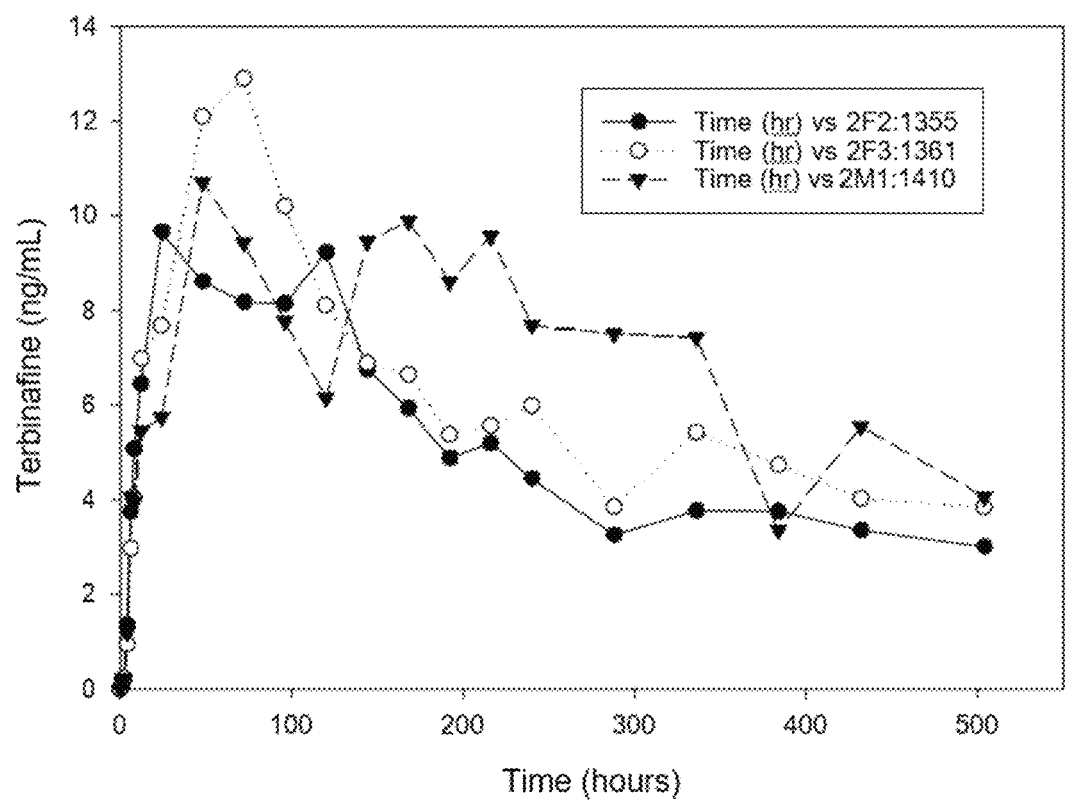
FIG. 5 is a graph depicting terbinafine plasma concentrations versus time after a single topical dose of approximately 42 mg/kg (ten application sites) Terbinafine applied directly to the skin to Hanford Miniature Swine.

The terbinafine plasma concentration-time profile for a single topical dose (ten application sites) of approximately 42 mg/kg terbinafine for two females and one male is presented in Table 8. A graph of the time versus terbinafine plasma concentrations is presented in FIG. 5.

TABLE 8

| Time (hr) | Animal # | | | Mean | SD |
| --- | --- | --- | --- | --- | --- |
| | 2F2: 1355 | 2F3: 1361 | 2M1: 1410 | | |
| 0 | <0.0200 | <0.0200 | <0.0200 | 0 | 0 |
| 1 | 0.0631 | 0.122 | 0.156 | 0.114 | 0.0384 |
| 2 | 0.195 | 0.225 | 0.218 | 0.213 | 0.0128 |
| 4 | 1.35 | 0.949 | 1.19 | 1.16 | 0.165 |
| 6 | 3.74 | 2.97 | 4.06 | 3.59 | 0.457 |
| 8 | 5.07 | 4.04 | 3.95 | 4.35 | 0.508 |
| 12 | 6.45 | 6.98 | 5.45 | 6.29 | 0.634 |
| 24 | 9.65 | 7.68 | 5.74 | 7.69 | 1.60 |
| 48 | 8.61 | 12.1 | 10.7 | 10.5 | 1.43 |
| 72 | 8.17 | 12.9 | 9.43 | 10.2 | 2.00 |
| 96 | 8.15 | 10.2 | 7.77 | 8.71 | 1.07 |
| 120 | 9.22 | 8.11 | 6.15 | 7.83 | 1.27 |
| 144 | 6.75 | 6.89 | 9.46 | 7.70 | 1.25 |
| 168 | 5.92 | 6.64 | 9.89 | 7.48 | 1.73 |
| 192 | 4.88 | 5.38 | 8.61 | 6.29 | 1.65 |
| 216 | 5.19 | 5.56 | 9.57 | 6.77 | 1.98 |
| 240 | 4.44 | 5.98 | 7.69 | 6.04 | 1.33 |
| 288 | 3.25 | 3.85 | 7.51 | 4.87 | 1.88 |
| 336 | 3.76 | 5.42 | 7.43 | 5.54 | 1.50 |
| 384 | 3.75 | 4.74 | 3.35 | 3.95 | 0.584 |
| 432 | 3.35 | 4.02 | 5.54 | 4.30 | 0.916 |
| 504 | 3.00 | 3.84 | 4.06 | 3.63 | 0.457 |

Figure 6:
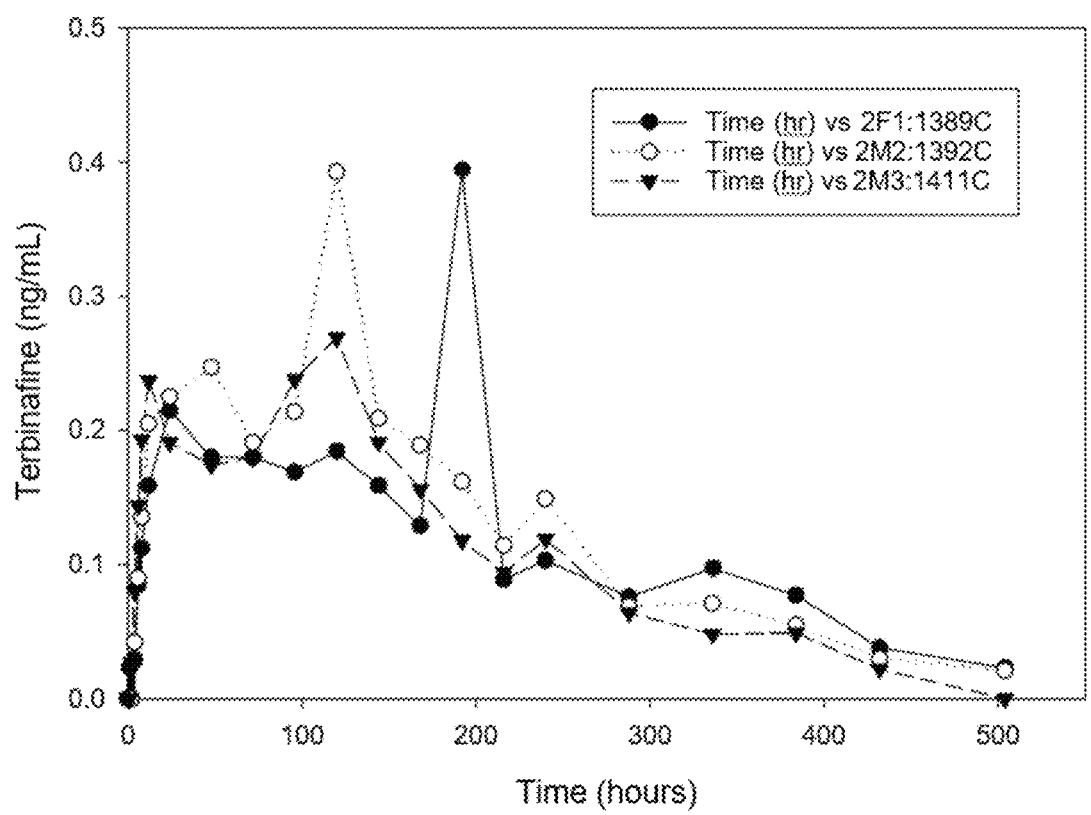
FIG. 6 is a graph depicting terbinafine plasma concentrations versus time after a single topical dose of approximately 42 mg/kg (ten application sites) Terbinafine applied in Hill Top Chambers to Hanford Miniature Swine.

The terbinafine plasma concentration-time profile for a single topical dose (ten application sites) of approximately 42 mg/kg terbinafine in Hill Top chambers for one female and two males is presented in Table 9. A graph of the time versus terbinafine plasma concentrations is presented in FIG. 6.

TABLE 9

| Time (hr) | Animal # | | | Mean | SD |
| --- | --- | --- | --- | --- | --- |
| | 2F1: 1389 | 2M2: 1392 | 2M3: 1411 | | |
| 0 | <0.0200 | <0.0200 | <0.0200 | 0 | NC |
| 1 | 0.0228 | <0.0200 | <0.0200 | 0.0228 | NC |
| 2 | <0.0200 | <0.0200 | 0.0268 | 0.0268 | NC |
| 4 | 0.0294 | 0.0423 | 0.0804 | 0.051 | 0.0216 |
| 6 | 0.0847 | 0.0896 | 0.144 | 0.106 | 0.0270 |
| 8 | 0.112 | 0.135 | 0.193 | 0.147 | 0.0341 |
| 12 | 0.159 | 0.205 | 0.237 | 0.200 | 0.0320 |
| 24 | 0.215 | 0.225 | 0.191 | 0.210 | 0.0143 |
| 48 | 0.180 | 0.247 | 0.174 | 0.200 | 0.0331 |
| 72 | 0.180 | 0.191 | 0.180 | 0.184 | 0.00519 |
| 96 | 0.169 | 0.214 | 0.238 | 0.207 | 0.0286 |
| 120 | 0.184 | 0.393 | 0.269 | 0.282 | 0.0858 |
| 144 | 0.159 | 0.209 | 0.191 | 0.186 | 0.0207 |
| 168 | 0.129 | 0.189 | 0.156 | 0.158 | 0.0245 |
| 192 | 0.394 | 0.162 | 0.118 | 0.225 | 0.121 |
| 216 | 0.0885 | 0.114 | 0.0937 | 0.0987 | 0.0110 |
| 240 | 0.103 | 0.149 | 0.119 | 0.124 | 0.019 |
| 288 | 0.0764 | 0.0686 | 0.0636 | 0.0695 | 0.00527 |
| 336 | 0.0973 | 0.0709 | 0.0483 | 0.0722 | 0.0200 |
| 384 | 0.0767 | 0.0551 | 0.0485 | 0.0601 | 0.0120 |
| 432 | 0.0379 | 0.0298 | 0.0224 | 0.030 | 0.00633 |
| 504 | 0.0231 | 0.0206 | <0.0200 | 0.0219 | NC |

Figure 7:
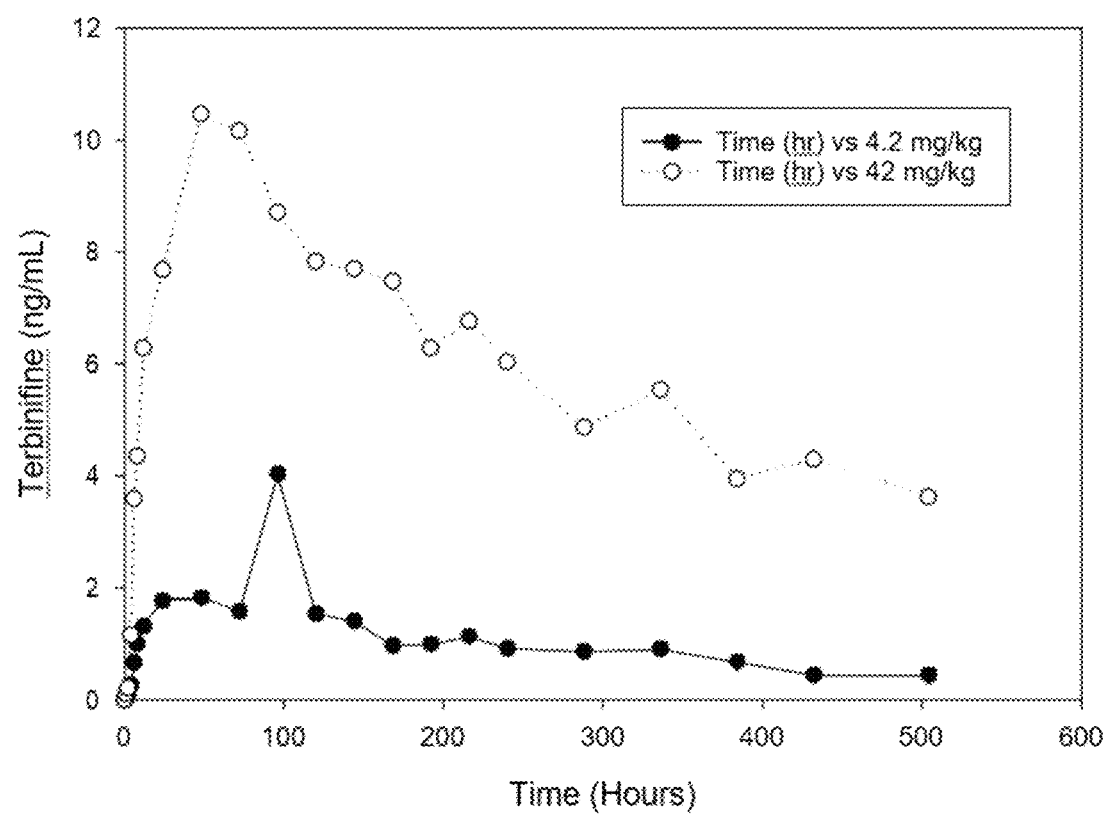
FIG. 7 is a graph depicting mean terbinafine plasma concentrations versus time after a single topical dose of approximately 4.2 mg/kg or 42 mg/kg Terbinafine applied directly to the skin to Hanford Miniature Swine.
Figure 8:
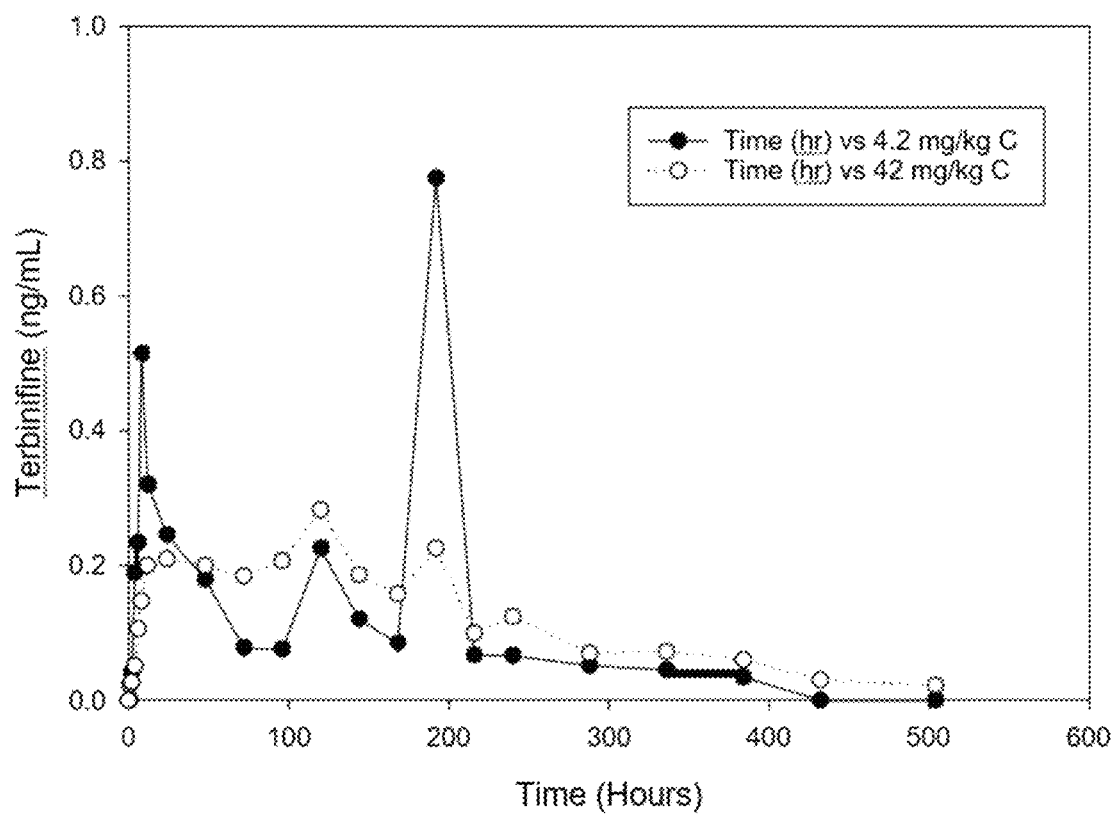
FIG. 8 is a graph depicting terbinafine plasma concentrations versus time after a single topical dose of approximately 4.2 mg/kg or 42 mg/kg Terbinafine applied in a Hill Top Chambers to Hanford Miniature Swine.

A graph of the time versus mean terbinafine plasma concentrations for 4.2 and 42 mg/kg terbinafine applied directly to the skin is presented in FIG. 7. A graph of the time versus mean terbinafine plasma concentrations for 4.2 and 42 mg/kg terbinafine applied in Hill Top chambers is presented in FIG. 8.

Pharmacokinetic Parameters: The volume of terbinafine applied directly to the skin was 171 μL (83.79 mg) and the volume added to the Hill Top chambers was 200 μL (98.0 mg). The weight of the individual animals varied from 21.4 kg to 30.3 kg. For the calculation of pharmacokinetic parameters that required a value for the dose, the actual dose that each animal received was calculated and presented in Table 10 below. No allowance was made for any dosing solution that may have been absorbed by the Hill Top chamber pad. Calculated terbinafine doses were used for pharmacokinetic parameter calculations.

TABLE 10

| Animal # | Treatment | Doses | Dose per application (mg) | Total Dose (mg) | Weight (kg) | Dose (mg/kg) |
| --- | --- | --- | --- | --- | --- | --- |
| 1M1: 1427 | Direct | 1 | 83.79 | 83.79 | 23.3 | 3.6 |
| 1M2: 1364 | Chamber | 1 | 98 | 98 | 23.9 | 4.1 |
| 1M3: 1419 | Chamber | 1 | 98 | 98 | 23.6 | 4.2 |
| 1F1: 1366 | Chamber | 1 | 98 | 98 | 31.6 | 3.1 |
| 1F2: 1430 | Direct | 1 | 83.79 | 83.79 | 22.2 | 3.8 |
| 1F3: 1429 | Direct | 1 | 83.79 | 83.79 | 21.5 | 3.9 |
| 2M1: 1410 | Direct | 10 | 83.79 | 837.9 | 28.4 | 29.5 |
| 2M2: 1392 | Chamber | 10 | 98 | 980 | 24.1 | 40.7 |
| 2M3: 1411 | Chamber | 10 | 98 | 980 | 22.5 | 43.6 |
| 2F1: 1389 | Chamber | 10 | 98 | 980 | 21.4 | 45.8 |
| 2F2: 1355 | Direct | 10 | 83.79 | 837.9 | 29.3 | 28.6 |
| 2F3: 1361 | Direct | 10 | 83.79 | 837.9 | 30.3 | 27.7 |

Pharmacokinetic parameter estimates for a single topical dose of approximately 4.2 mg/kg terbinafine for two females and one male is presented in Table 11 below.

TABLE 11

| Parameter | 1F2: 1430 | 1F3: 1429 | 1M1: 1427 | Mean | SD |
| --- | --- | --- | --- | --- | --- |
| Rsq_adjusted | 0.872 | 0.981 | 0.805 | NC | NC |
| No. points used for $t_{1/2}$ | 14 | 3 | 11 | NC | NC |
| $t_{1/2}$ (hr) | 158.9 | 136.5 | 293.4 | 196.3 | 69.3 |
| $T_{max}$ (hr) | 48 | 48 | 96 | NC | NC |
| $C_{max}$ (ng/mL) | 1.14 | 2.89 | 9.07 | 4.37 | 3.40 |
| $T_{last}$ (hr) | 504 | 504 | 504 | NC | NC |
| $AUC_{0-last}$ (ng*hr/mL) | 237.6 | 658.3 | 789.7 | 561.8 | 235.5 |
| $AUC_{0-\infty}$ (ng*hr/mL) | 277.2 | 738.0 | 1,097 | 703.9 | 335.3 |
| $AUC_{0-\infty}$/Dose (hr*kg*ng/mL/mg) | 73.0 | 189.2 | 304.6 | 188.9 | 94.6 |
| AUC extrapolated (%) | 14.3 | 10.8 | 28.0 | NC | NC |

Pharmacokinetic parameter estimates for a single topical dose of approximately 4.2 mg/kg terbinafine in Hill Top chambers for one female and two males is presented in Table 12 below.

TABLE 12

| Parameter | 1F1: 1366 | 1M2: 1364 | 1M3: 1419 | Mean | SD |
| --- | --- | --- | --- | --- | --- |
| Rsq_adjusted | Missing | 0.995 | 0.997 | NC | NC |
| No. points used for $t_{1/2}$ | 0 | 3 | 3 | NC | NC |
| $t_{1/2}$ (hr) | Missing | 22.1 | 248.0 | 135.1 | NC |
| $T_{max}$ (hr) | 192 | 120 | 192 | NC | NC |
| $C_{max}$ (ng/mL) | 1.58 | 0.205 | 0.725 | 0.84 | 0.57 |
| $T_{last}$ (hr) | 384 | 192 | 384 | NC | NC |
| $AUC_{0-last}$ (ng*hr/mL) | 43.8 | 9.37 | 75.9 | 43.0 | 27.2 |
| $AUC_{0-\infty}$ (ng*hr/mL) | Missing | 10.0 | 89.8 | 49.9 | NC |
| $AUC_{0-\infty}$/Dose (hr*kg*ng/mL/mg) | Missing | 2.4 | 21.4 | 11.9 | NC |
| AUC extrapolated (%) | Missing | 6.7 | 15.5 | NC | NC |

Pharmacokinetic parameter estimates for a single topical dose of approximately 42 mg/kg terbinafine for two females and one male is presented in Table 13 below.

TABLE 13

| Parameter | 2F2: 1355 | 2F3: 1361 | 2M1: 1410 | Mean | SD |
|---|---|---|---|---|---|
| Rsq_adjusted | 0.971 | 0.862 | 0.714 | NC | NC |
| No. points used for $t_{1/2}$ | 3 | 4 | 10 | NC | NC |
| $t_{1/2}$ (hr) | 378.0 | 329.9 | 258.3 | 322.1 | 49.2 |
| $T_{max}$ (hr) | 24 | 72 | 48 | NC | NC |
| $C_{max}$ (ng/mL) | 9.65 | 12.9 | 10.7 | 11.1 | 1.35 |
| $T_{last}$ (hr) | 504 | 504 | 504 | NC | NC |
| $AUC_{0\text{-}last}$ (ng*hr/mL) | 2,602 | 3,108 | 3,521 | 3,077 | 375.9 |
| $AUC_{0\text{-}\infty}$ (ng*hr/mL) | 4,238 | 4,936 | 5,034 | 4,736 | 354.6 |
| $AUC_{0\text{-}\infty}$/Dose (hr*kg*ng/mL/mg) | 148.2 | 178.2 | 170.6 | 165.7 | 12.8 |
| AUC extrapolated (%) | 38.6 | 37.0 | 30.1 | NC | NC |

Pharmacokinetic parameter estimates for a single topical dose of approximately 42 mg/kg terbinafine in Hill Top chambers for one female and two males is presented in Table 14 below.

TABLE 14

| Parameter | 2F1: 1389 | 2M2: 1392 | 2M3: 1411 | Mean | SD |
|---|---|---|---|---|---|
| Rsq_adjusted | 0.953 | 0.960 | 0.941 | NC | NC |
| No. points used for $t_{1/2}$ | 4 | 10 | 10 | NC | NC |
| $t_{1/2}$ (hr) | 76.6 | 108.1 | 99.5 | 94.7 | 13.3 |
| $T_{max}$ (hr) | 192 | 120 | 120 | NC | NC |
| $C_{max}$ (ng/mL) | 0.394 | 0.393 | 0.269 | 0.35 | 0.06 |
| $T_{last}$ (hr) | 504 | 504 | 432 | NC | NC |
| $AUC_{0\text{-}last}$ (ng*hr/mL) | 60.2 | 64.9 | 53.0 | 59.4 | 4.9 |
| $AUC_{0\text{-}\infty}$ (ng*hr/mL) | 62.7 | 68.2 | 56.2 | 62.4 | 4.9 |
| $AUC_{0\text{-}\infty}$/Dose (hr*kg*ng/mL/mg) | 1.4 | 1.7 | 1.3 | 1.4 | 0.2 |
| AUC extrapolated | 4.1 | 4.8 | 5.6 | NC | NC |

A comparison of the mean pharmacokinetic parameter estimates for each dose group, including a calculation of the ratios of the high dose/low dose parameters is presented in Table 15 below.

TABLE 15

| | Applied to the skin | | | Applied in Hill Top C 42hambers | | |
|---|---|---|---|---|---|---|
| Parameter | 4.2 mg/kg | 42 mg/kg | High/low | 4.2 mg/kg | mg/kg | High/low |
| $t_{1/2}$ (hr) | 196.3 | 322.1 | 1.64 | 135.1 | 94.7 | 0.70 |
| $C_{max}$ (ng/mL) | 4.37 | 11.1 | 2.54 | 0.84 | 0.35 | 0.42 |
| $AUC_{0\text{-}last}$ (ng*hr/mL) | 561.8 | 3,077 | 5.48 | 43.0 | 59.4 | 1.38 |
| $AUC_{0\text{-}\infty}$ (ng*hr/mL) | 703.9 | 4,736 | 6.73 | 49.9 | 62.4 | 1.25 |
| $AUC_{0\text{-}\infty}$/Dose (hr*kg*ng/mL/mg) | 188.9 | 165.7 | 0.88 | 11.9 | 1.4 | 0.12 |

Comparison topical versus oral administration: Oral administration of a single 250-mg terbinafine tablet (Lamisil®) in human results in peak plasma concentrations of approximately 0.97-1.5 ug/mL within 2 hours after administration. The terminal half-life of 200-400 hours is a result of the slow elimination of terbinafine from tissues such as skin and adipose. The $AUC_{48h}$ is 4506 ng·hr/mL. The absorption of topical high-dose terbinafine as described above was slow with $T_{max}$ occurring between 24 to 96 hours. Consistent with topical Lamisil, penetration of terbinafine from a topical high-dose terbinafine into the systemic circulation was minimal. The $C_{max}$ and $AUC_{0\text{-}inf}$ increased between the 4.2 and 42 mg/kg dose groups applied directly to the skin but not dose proportional. The terminal half-life was long and ranged between 196 to 322 hours. For purpose of comparison to the same topical dose of high-dose terbinafine (4.2 mg/kg), a single oral 250-mg Lamisil® tablet (4.2 mg/kg) results in peak plasma concentrations of 1000 ng/mL within 2 hours after administration; the AUC is approximately 4560 ng·h/mL.

Remarkably, a single 4.2 mg/kg topical dose of the high-concentration formulation described above resulted in three minipigs in a 227-fold lower mean peak plasma concentration (4.4 ng/mL) compared to the same human oral dose. Peak plasma concentration from the topical dose occurred within 48-96 hours after administration, $AUC_{504\,h}$ of 562 ng·hr/mL, and slow mean terminal half-life of approximately 200 hours was observed. Similarly, a larger 42 mg/kg topical dose of HSG applied over a 10-fold greater body surface compared to the lower dose group resulted in mean peak plasma concentration of 11.1 ng/mL and $AUC_{504\,h}$ of 3,077 ng·hr/mL. Slow absorption (24-72 hours) and long mean terminal half-life (322 hours) was shown. The 10-fold increase in surface area and applied dose resulted in a less than proportional increase in system $C_{max}$ and AUC.

As can be seen from the above data, topical/subungual administration of even high-dose formulations will advantageously avoid systemic exposure levels of terbinafine as would otherwise be observed upon oral delivery. Moreover, the high-dose formulations can be administered to the subungual space and will distribute throughout substantially the entire subungual space due to the flowability (while at the same time being retained within the subungual space). Owing to the high concentration, terbinafine can then diffuse beyond the subungual space at concentrations above MIC into a much larger treatment space that includes the nail plate and nail bed. In addition, due to the high concentrations that can be achieved in the nail plate, terbinafine will be present at or above MIC in the distally advancing nail plate and as such present a barrier to fungal growth, leading ultimately to replacement of diseased nail tissue with healthy nail.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A high-concentration antifungal liquid pharmaceutical composition, comprising:
   a pharmaceutically acceptable carrier comprising a hydrophobic solvent, an optional hydrophilic solvent, an optional polymeric film forming agent, and an antifungal agent at a high concentration of at least 40 wt % of the composition, wherein the antifungal agent is terbinafine;
   wherein the antifungal agent is dissolved in the pharmaceutically acceptable carrier and is stable for at least 4 weeks when the composition is stored at 25° C. and 60% relative humidity; and
   wherein the pharmaceutical composition has a viscosity of between about 500-2,500 cP (mPa*s).

2. The high-concentration antifungal composition of claim 1, wherein the antifungal agent is stable for at least 3 months when the composition is stored at 25° C. and 60% relative humidity.

3. The high-concentration antifungal composition of claim 1, wherein the hydrophobic solvent is selected from the group consisting of isostearic acid, benzyl alcohol, diisopropyl adipate, diethyl sebacate, isopropyl myristate, and combinations thereof.

4. The high-concentration antifungal composition of claim 1, wherein the hydrophobic solvent comprises isopropyl myristate.

5. The high-concentration antifungal composition of claim 4, wherein the isopropyl myristate present in the composition in an amount of at least 25 wt. % based on a total weight of the composition.

6. The high-concentration antifungal composition of claim 4, wherein the hydrophobic solvent further comprises diisopropyl adipate, benzyl alcohol, or a combination thereof.

7. The high-concentration antifungal composition of claim 1, wherein the pharmaceutically acceptable carrier comprises the hydrophilic solvent and wherein the hydrophilic solvent is selected from the group consisting of dimethyl isosorbide, propylene carbonate, D,L-lactic acid, and combinations thereof.

8. The high-concentration antifungal composition of claim 1, wherein the pharmaceutically acceptable carrier comprises the polymeric film forming agent.

9. The high-concentration antifungal composition of claim 8 wherein the polymeric film forming agent comprises a substituted cellulose.

10. The high-concentration antifungal composition of claim 9, wherein the substituted cellulose comprises ethyl cellulose.

11. The high-concentration antifungal composition of claim 8, wherein the polymeric film forming agent is present in the composition in an amount of at least 2 wt. % based on a total weight of the composition.

12. The high-concentration antifungal composition of claim 1, wherein the antifungal agent is terbinafine free base, and/or wherein the pharmaceutical composition has a viscosity of less than 2,500 and at least 1,000 cP (mPa*s).

13. A method of treating a subungual space in a mammal, comprising:
    administering a high-concentration antifungal liquid pharmaceutical composition according to claim 1 to a subungual space located between the nail plate and the nail bed, wherein the antifungal agent has a concentration of at least 40 wt % of the composition;
    wherein the composition, upon subungual administration, produces a minimum inhibitory concentration of the therapeutic agent in the subungual space and a treatment space that extends beyond the subungual space.

14. The method of claim 13, wherein the step of administering the composition comprises inserting a cannula between the nail plate and the nail bed and administering the composition through the cannula.

15. The method of claim 14, wherein the cannula is a blunt-tip cannula having at least one lateral opening in a distal portion of the cannula.

16. The method of claim 13, wherein the step of administering the composition comprises injecting between 10 and 100 μL into the subungual space.

17. The method of claim 13, wherein the step of administering the composition is atraumatic.

* * * * *